US010281534B2

(12) United States Patent
Tramm et al.

(10) Patent No.: US 10,281,534 B2
(45) Date of Patent: May 7, 2019

(54) TISSUE-SLICE MRI COIL AND ROTATION MECHANISM

(71) Applicant: Life Services LLC, Minneapolis, MN (US)

(72) Inventors: Brandon J. Tramm, Otsego, MN (US); Scott M. Schillak, Minneapolis, MN (US); Matthew T. Waks, Coon Rapids, MN (US); Charles A. Lemaire, Apple Valley, MN (US)

(73) Assignee: Life Services, LLC, Minneapolis, MN (US)

( * ) Notice: Subject to any disclaimer, the term of this patent is extended or adjusted under 35 U.S.C. 154(b) by 1074 days.

(21) Appl. No.: 14/664,735

(22) Filed: Mar. 20, 2015

(65) Prior Publication Data

US 2015/0268315 A1 Sep. 24, 2015

Related U.S. Application Data

(60) Provisional application No. 61/968,358, filed on Mar. 20, 2014.

(51) Int. Cl.
*G01R 33/30* (2006.01)
*G01R 33/54* (2006.01)
(Continued)

(52) U.S. Cl.
CPC .......... *G01R 33/307* (2013.01); *G01N 24/08* (2013.01); *G01R 33/3415* (2013.01); *G01R 33/58* (2013.01); *G01R 33/31* (2013.01)

(58) Field of Classification Search
None
See application file for complete search history.

(56) References Cited

U.S. PATENT DOCUMENTS 4,801,553 A  1/1989 Owen et al.
4,885,539 A  12/1989 Roemer et al.
(Continued)

FOREIGN PATENT DOCUMENTS

WO  WO 2000037918  6/2000

OTHER PUBLICATIONS

Augustine, George J., "Combining Patch-clamp and Optical Methods in Brain Slices", "Journal of Neuroscience Methods", 1994, pp. 163-169, vol. 54, Publisher: Elsevier.
(Continued)

*Primary Examiner* — Patrick Assouad
*Assistant Examiner* — Suresh K Rajaputra
(74) *Attorney, Agent, or Firm* — Charles A. Lemaire; Jonathan M. Rixen; Lemaire Patent Law Firm, P.L.L.C.

(57) ABSTRACT

A method and apparatus for transmitting and receiving RF signals suitable for MRI and/or MRS from MR "coils" (antennae) that are arranged in an array next to a tissue-sample-slice holder that constrains the front, back, and edges of the tissue sample and is configured to rotate in a "roll" direction (about an axis parallel to the main DC magnetic field) and optionally also rotate in a pitch direction (at varying angles up and down, left-to-right, or both, relative to the roll axis and thus to the main DC magnetic field); the system optionally includes temperature control (heat and/or cooling), an optical grid that is marked or etched into a cover glass that holds the sample (in some embodiments, the grid is visible in the MRI images as well), an electrical and/or optical stimulation means for delivering stimulation Some embodiments combine optical image data with MR image data.

24 Claims, 10 Drawing Sheets

(51) Int. Cl.
  *G01R 33/465* (2006.01)
  *G01R 33/31* (2006.01)
  *G01R 33/36* (2006.01)
  *G01R 33/34* (2006.01)
  *G01N 24/08* (2006.01)
  *G01R 33/3415* (2006.01)
  *G01R 33/58* (2006.01)

(56) References Cited

U.S. PATENT DOCUMENTS

| | | | |
|---|---|---|---|
| 5,416,414 A * | 5/1995 | Mansfield | G01R 33/30 |
| | | | 324/318 |
| 5,480,482 A | 1/1996 | Novinson | |
| 5,665,398 A | 9/1997 | McCormick | |
| 5,836,877 A | 11/1998 | Zavislan | |
| 6,300,761 B1 | 10/2001 | Hagen et al. | |
| 6,534,983 B1 * | 3/2003 | Boskamp | G01R 33/3415 |
| | | | 324/318 |
| 6,538,441 B1 | 3/2003 | Watkins et al. | |
| 6,675,037 B1 * | 1/2004 | Tsekos | A61B 5/0555 |
| | | | 600/417 |
| 6,822,448 B2 | 11/2004 | Watkins et al. | |
| 6,834,238 B1 | 12/2004 | Hochman | |
| 6,989,674 B2 * | 1/2006 | Wind | G01R 33/307 |
| | | | 324/318 |
| 7,295,870 B2 | 11/2007 | Allain et al. | |
| 7,474,098 B2 | 1/2009 | King | |
| 8,299,681 B2 | 10/2012 | Snyder et al. | |
| 8,632,577 B1 | 1/2014 | Bendett et al. | |
| 8,674,695 B2 | 3/2014 | Wiggins | |
| 8,784,461 B2 | 7/2014 | Webb et al. | |
| 8,788,044 B2 | 7/2014 | John | |
| 2008/0116889 A1 * | 5/2008 | Hu | G01R 33/46 |
| | | | 324/309 |
| 2010/0160816 A1 * | 6/2010 | Parihar | A61B 10/0275 |
| | | | 600/564 |
| 2012/0265051 A1 * | 10/2012 | Fischer | A61B 10/0241 |
| | | | 600/411 |

OTHER PUBLICATIONS

Roemer, et al., "The NMR Phased Array", "Magnetic Resonance in Medicine", 1990, pp. 192-225, vol. 16.

Wiggins, et al., "96-Channel Receive-Only Head Coil for 3 Tesla: Design Optimization and Evaluation", "Magn. Reson. Med.", Sep. 2009, pp. 754-762, vol. 62, No. 3.

* cited by examiner

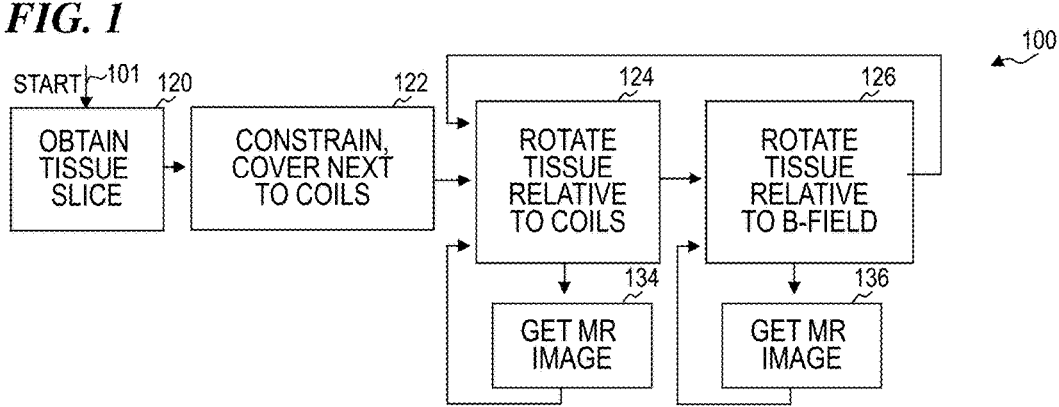
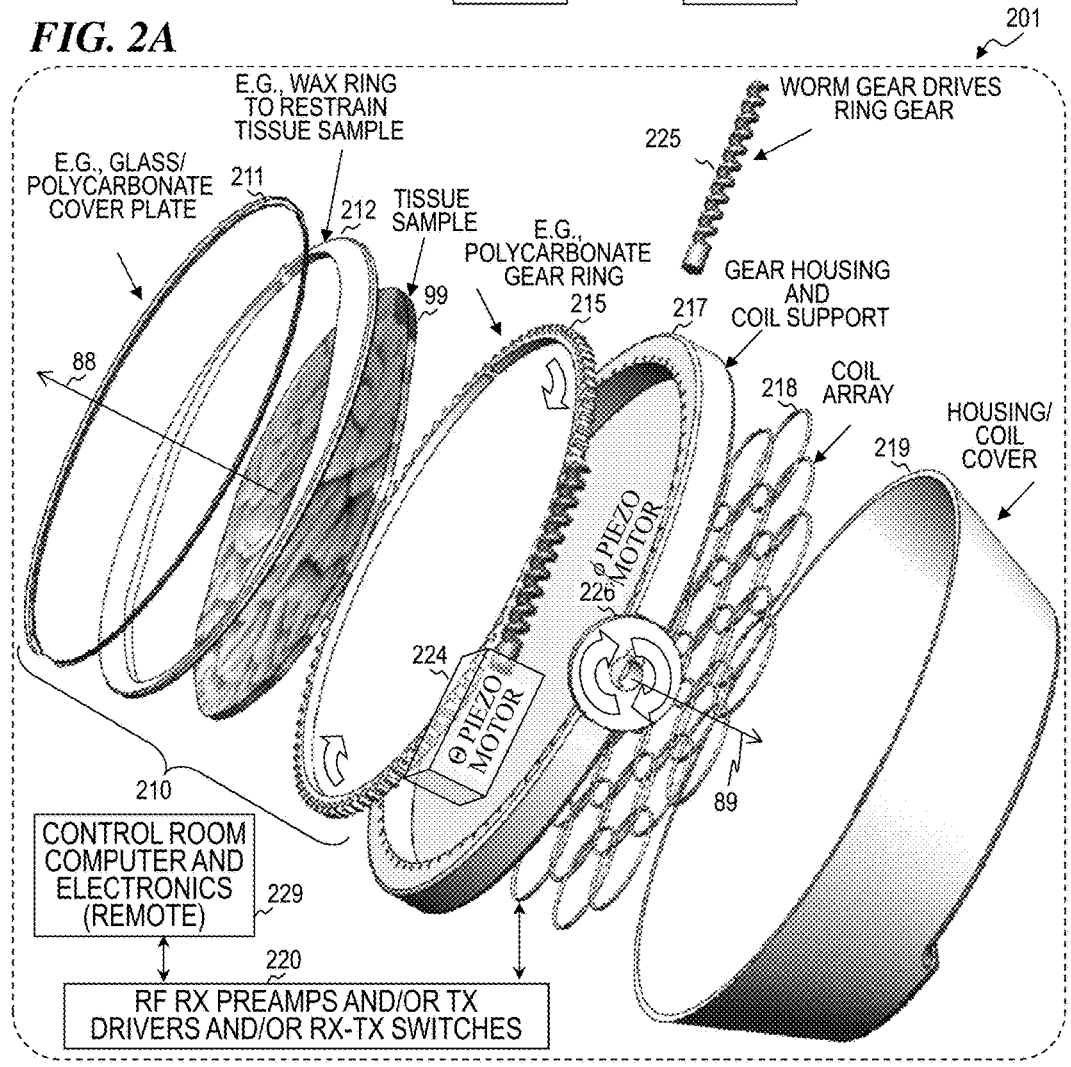

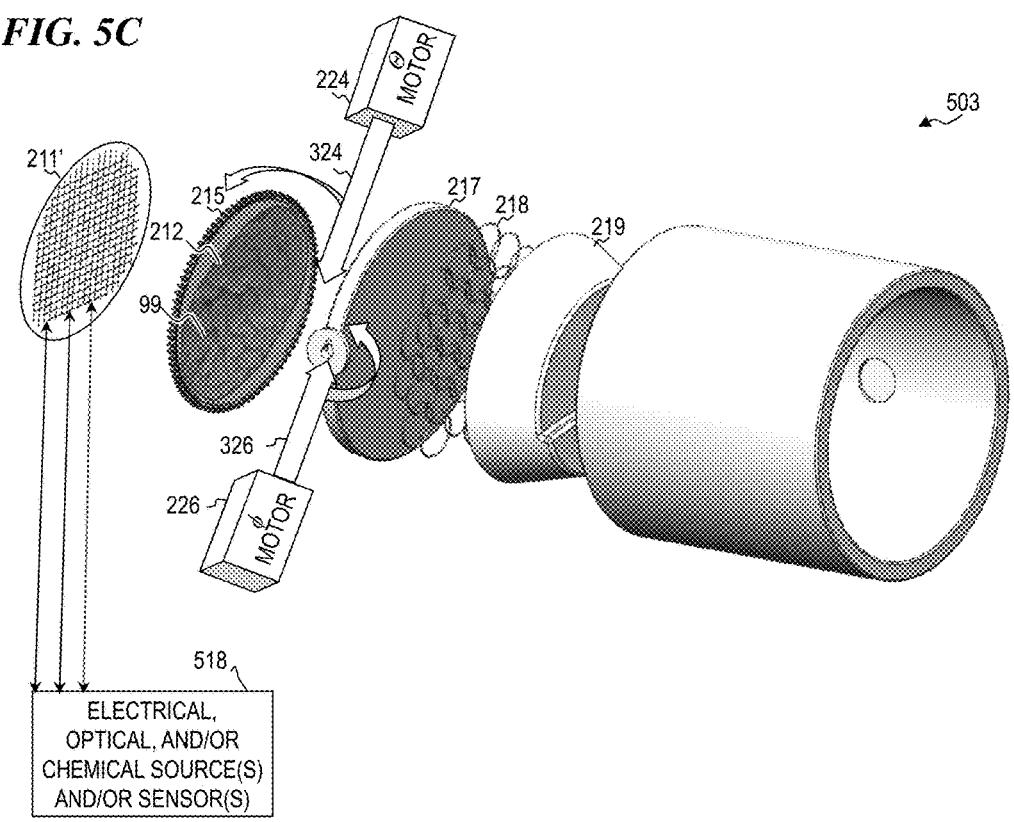

TISSUE-SLICE MRI COIL AND ROTATION MECHANISM

RELATED APPLICATIONS

This invention claims priority benefit under 35 U.S.C. § 119(e) of U.S. Provisional Patent Application No. 61/968,358 filed Mar. 20, 2014 by Brandon J. Tramm et al., titled "TISSUE-SLICE MRI COIL AND ROTATION MECHANISM," which is incorporated herein by reference in its entirety.

FIELD OF THE INVENTION

This invention relates to the field of magnetic-resonance imaging (MRI) and magnetic-resonance spectroscopy (MRS), and more specifically to a method and apparatus for transmitting (TX) and receiving (RX) radio-frequency (RF) signals suitable for MRI and/or MRS from MRI "coils" (antennae) that are arranged in an array next to a tissue-sample-slice holder that constrains the front, back, and edges of the tissue sample and is configured to rotate in a "roll" direction (about a roll axis that is parallel to the main DC magnetic field) and optionally also rotate in a pitch and/or yaw direction (at varying angles up-and-down and/or side-to-side relative to the roll axis and thus to the main DC magnetic field); the system optionally includes temperature control (heat and/or cooling), an optical grid that is marked or etched into a cover glass that holds the sample (in some embodiments, the grid is visible in the MRI images as well), and/or an electrical- and/or optical-stimulation means for delivering physiological stimulation to the sample.

BACKGROUND OF THE INVENTION

Human tissue is often sliced to facilitate pathological examination. In one method, fixed or unfixed tissue may be frozen and sliced using a microtome mounted in a refrigeration device known as a cryostat, thus generating histological slices. For examination under an optical or electron microscope, the histological tissue slices may be mounted on a glass slide and may be stained to enhance the contrast between different tissues. Unfixed tissue sections can also be used for studies requiring enzyme localization in tissues and cells, or studies that use electrical and/or optical stimulation of the tissue to determine the result of such stimulation.

U.S. Pat. No. 4,801,553 to Owen et al. issued on Jan. 31, 1989 with the title "Methods of and apparatus for preparing tissue specimens" and is incorporated herein by reference. This patent describes a cassette for holding a tissue specimen, the cassette including a body portion and a separable portion which snap together to enclose a specimen in a mould space in a mould space of the cassette. The specimen is located and oriented in the mould space between a compliant base portion and the separable portion. The specimen is processed by the successive application of processing fluids before being embedded in paraffin wax. During embedding, molten wax is supplied to a container in which the cassette is placed. Wax surrounds and embeds the specimen, the container base is then cooled to solidify a base layer of wax, allowing the remaining wax to be drained from the container, leaving the wax within the cassette to solidify and cool. After removal of the cassette from the container, portions of the cassette are stripped away to leave the embedded specimen ready for microtome sectioning.

U.S. Pat. No. 5,480,482 issued to Novinson on Jan. 2, 1996 titled "Reversible thermochromic pigments" and is incorporated herein by reference. U.S. Pat. No. 5,480,482 describes a color-changing pigment composition which changes color reversibly when heated comprising (a) a cyclic aryl lactone dye, (b) a diaminoalkane activator and (c) an ester. The pigment composition can also include a white pigment such as titanium dioxide as an opacifier or a yellow dye such Hansa yellow G. The pigment composition changes from a dark color, e.g., blue, to white when the composition is heated to a specified temperature, e.g., to a temperature of 52 degrees C., and reversibly changes from white back to the blue color when the pigment composition is cooled, e.g., to a temperature below about 25 degrees C.

U.S. Pat. No. 5,665,398 to McCormick issued on Sep. 9 1997 with the title "Apparatus for embedding tissue samples", and is incorporated herein by reference. U.S. Pat. No. 5,665,398 describes a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette. The system includes means for dispensing a predetermined amount of molten wax into the embedding mold.

U.S. Pat. No. 5,836,877 to Zavislan issued on Nov. 17, 1998 with the title "System for facilitating pathological examination of a lesion in tissue" and is incorporated herein by reference. U.S. Pat. No. 5,836,877 describes having both a camera for producing a digital macroscopic picture of the lesion and an imager are coupled to a computer system. The imager is responsive to the computer system and has optics for scanning the lesion to generate images representing microscopic sections of the lesion which provide sufficient information for pathological examination of the lesion. The computer system generates location information, referencing the location in the macroscopic picture of the lesion where the lesion was scanned to the images, and stores data in an electronic file structure which contains at least a representation of the images, a representation of the macroscopic picture, and the location information. The file structure may then be sent to another computer system for viewing the images stored in the file structure to facilitate pathological examination of the lesion by persons trained to interpret such images, adding a diagnostic report about the lesion to the data of the file structure, and sending back the file structure to the computer system that originated it.

United States Patent Application 20030091980 to Lynch et al. published on May 15, 2003 with the title "Detection and characterization of psychoactives using analysis of network level physiological responses in a neuronal sample" and is incorporated herein by reference. This Application 20030091980 describes methods and devices for the detection and characterization of psychoactive compounds by analyzing alterations of network level physiological characteristics before and after the introduction of a candidate sample onto an in vitro neuronal tissue sample. The application also describes a software package that enables an operator to deliver a timed electrical pulse to neuronal samples at a specific point in their spontaneous or induced oscillations. Such temporal stimulations trigger unexpected and useful network level physiological responses.

U.S. Pat. No. 6,834,238 to Hochman issued on Dec. 21 2004 with the title "Method for identifying optical contrast enhancing agents" and is incorporated herein by reference. U.S. Pat. No. 6,834,238 describes optical detection techniques for the assessment of the physiological state, health and/or viability of biological materials. Biological materials which may be examined using such techniques include cells, tissues, organs and subcellular components. The techniques may be employed in high throughput screening of potential diagnostic and/or therapeutic agents. Slices of tissue or tumors may be maintained under culture conditions for prolonged periods of time and assessed according to methods of the present invention.

Low-power circuits can use varactors (electrically variable capacitors), field-effect transistors (used as variable gain elements or variable resistors) and like components that are directly electrically-adjustable, for use in adjusting frequency, impedance or other circuit characteristics and parameters, however such components are often unsuitable or inoperative in high fields.

U.S. Pat. No. 8,299,681 issued Oct. 30, 2012 with the title "Remotely adjustable reactive and resistive electrical elements and method" and is incorporated herein by reference. U.S. Pat. No. 8,299,681 describes an apparatus and method that includes providing a variable-parameter electrical component in a high-field environment and based on an electrical signal, automatically moving a movable portion of the electrical component in relation to another portion of the electrical component to vary at least one of its parameters. In some embodiments, the moving uses a mechanical movement device (e.g., a linear positioner, rotary motor, or pump). In some embodiments of the method, the electrical component has a variable inductance, capacitance, and/or resistance. Some embodiments include using a computer that controls the moving of the movable portion of the electrical component in order to vary an electrical parameter of the electrical component. Some embodiments include using a feedback signal to provide feedback control in order to adjust and/or maintain the electrical parameter. Some embodiments include a non-magnetic positioner connected to an electrical component configured to have its RLC parameters varied by the positioner.

U.S. Pat. No. 8,674,695 issued Mar. 18, 2014 to Wiggins with the title "Radio Frequency Coil Arrangement for High Field Magnetic Resonance Imaging with Optimized Transmit and Receive Efficiency for a Specified Region of Interest, and Related System and Method," and is incorporated herein by reference. In the application, Wiggins describes exemplary embodiments of a coil arrangement that can include, e.g., a plurality of elements which can be provided at an angle from one another. The angle can be selected to effectuate an imaging of a target region of interest at least one of a predetermined depth or range of depths, for example. In certain exemplary embodiments according to the present disclosure, the angle can be selected to effectuate an exemplary predetermined transmit efficiency for at least one of the elements. Additionally, the exemplary angle can be selected to effectuate a predetermined receive sensitivity for at least one of the elements. Further, according to certain exemplary embodiments of a coil arrangement in according to the present disclosure, the angle can be adjusted manually and/or automatically.

A journal article, "96-Channel Receive-Only Head Coil for 3 Tesla: Design Optimization and Evaluation" by Graham C. Wiggins et al. (Magn. Reson. Med. 2009 September; 62(3): 754-762. doi:10.1002/mrm.22028), describes a receive coil, and is incorporated herein by reference.

U.S. Pat. No. 4,885,539 to Roemer et al. issued Dec. 5, 1989 with the title "Volume NMR coil for optimum signal-to-noise ratio" and is incorporated herein by reference. In U.S. Pat. No. 4,885,539, Roemer et al. describe an RF volume coil with optimized signal-to-noise ratio, for NMR use, has a reduced length $L_c$, which is between about $0.3r_s$ and about $1.5r_s$, where $r_s$ is the radius of a sample-to-be-investigated, contained within the cylindrical volume coil, with the volume coil radius $r_c$ being between about $1.0r_s$ and about $1.6r_s$ the "short" volume coil has an improved SNR for a voxel located substantially on the central plane of the coil, relative to the SNR of a "normal"-length volume coil with $L_c$ greater or equal to $4r_s$.

A journal article, "The NMR Phased Array" by P. B. Roemer et al. (Magn. Reson. Med. 1990 November; Vol. 16 Issue 262 pages 192-225) describes a phased array receive coil, and is incorporated herein by reference. Roemer et al. describe ways to overlap coil loops (circular loops overlapped by spacing the centers of the circular loops at 0.75 diameter, and square loops by about 0.9 diameter; and the loops are all the same size) to reduce mutual-induction interference.

U.S. Pat. No. 6,534,983 to Boskamp et al. issued Mar. 18, 2003 with the title "Multi-channel phased array coils having minimum mutual inductance for magnetic resonance systems" and is incorporated herein by reference. In U.S. Pat. No. 6,534,983, Boskamp et al. describe a multi-channel phased array coil for use in a magnetic resonance (MR) system is disclosed herein. The phased array coil includes N coils configured in an array, each of the N coils having a geometric shape and overlapping with (N−1) coils to form an overlap area within the array. The geometric shape of each of the coils and the overlap area are configured to cause a mutual inductance between every pair of the coils to be less than 10 percent of the self-inductance of each of the N coils. At least four coils are provided in the phased array coil.

U.S. Pat. No. 6,538,441 issued to Watkins et al. on Mar. 25, 2003 with the title "RF coil for reduced electric field exposure for use in very high field magnetic resonance imaging" and is incorporated herein by reference. In U.S. Pat. No. 6,538,441, Watkins et al. describe an RF coil assembly for a very high field Magnetic Resonance Imaging (MRI) system is provided. The RF coil assembly comprises a plurality of conductors arranged cylindrically and disposed about a patient bore tube of the MRI system. Each of the conductors is configured for the RF coil assembly to resonate at substantially high frequencies. Further, the RF coil assembly comprises a plurality of capacitive elements disposed between and connecting respective ends of the conductors and further disposed in a spaced-apart relationship with the patient bore tube. The capacitive elements are for electrically interconnecting the plurality of conductors at the respective ends of the conductors.

U.S. Pat. No. 6,822,448 issued to Watkins et al. on Nov. 23, 2004 with the title "RF coil for very high field magnetic resonance" and is incorporated herein by reference. In U.S. Pat. No. 6,822,448, Watkins et al. describe an RF coil assembly for a very high field Magnetic Resonance Imaging (MRI) system is provided comprising a plurality of conductors arranged cylindrically and disposed about a cylindrical patient bore tube of the MRI system and a plurality of capacitive elements for electrically interconnecting the plurality of conductors at respective ends of the conductors. The conductors have a width selected for the RF coil assembly to resonate at substantially high frequencies. A very high field Magnetic Resonance Imaging (MRI) system is provided that comprises a RF coil assembly adapted to resonate at substantially high frequencies, a RF coil shield assembly and a plurality of RF drive power cables.

U.S. Pat. No. 8,788,044 to John issued on Jul. 22 2014 with the title "Systems and methods for tissue stimulation in medical treatment" and is incorporated herein by reference.

This patent describes stimulation treatments for various medical disorders, such as neurological disorders, that include systems, strategies, and methods for providing TMS, electrical, magnetic, optical and other stimulation. Some stimulation methods comprise varying the stimulation parameters to improve the therapeutic efficacy of stimulation, and decrease risk of habituation and side-effects such as interference with normal brain, sensory, motor, and cognitive processes. The creation, and subsequent variation, of stimulation parameters can use sensed data in order to match, adjust, or avoid matching characteristics of the stimulation therapy relative to certain endogenous brain activities. Novel methods are described for choosing, creating and subsequently stimulating with partial signals which summate to produce therapeutic vector fields having unique temporal patterns and low- or high-frequency spectral content.

A journal article by G. J. Augustine titled "Combining patch clamp and optical methods in brain slices," Journal of Neuroscience methods 54 (1994) pp. 163-169, is incorporated herein by reference. This article describes that combining patch-clamp and optical imaging techniques in brain slices offers several advantages for physiological studies of nerve cells. Numerous practical considerations weigh heavily in this design of an apparatus suitable for such combined measurements. These considerations include the thickness of the slices, the type of microscope to be used for imaging and the kind of optical signal to be measured. A system that combine optical and patch-clamp methods can be modified readily to permit studies of intracellular and extracellular signaling pathways via flash photolysis of caged compounds. U.S. Pat. No. 7,295,870 to Allain et al. issued on Nov. 13, 2007 with the title "Method for the detection and automatic characterization of nodules in a tomographic image and a system of medical imaging by tomodensimetry" and is incorporated herein by reference. This patent describes automatic detection and characterization of nodules in a tomographic image of an anatomical zone of a patient. The image is segmented for identifying therein a region of interest, and the segmented image is processed for identifying the nodule. During the processing step, an ellipsoid inscribed in the region of interest is modeled for deciding whether the image elements inscribed in this ellipsoid correspond to a nodule, and, for each zone of the region of interest extending beyond the ellipsoid, the image elements are identified which do not belong to the module according to mathematical morphologic criteria.

United States Patent Application Publication 20070236490 by Casteele et al. published on Oct. 11, 2007 with the title "Medical image display and review system" and is incorporated herein by reference. This publication 20070236490 describes an image display and review system for display of medical images represented by a digital image data set wherein a pre-defined number of viewports for display of different image representations is provided and wherein at least some of these viewports are configured to enable sequential display of different image representations deduced from the digital image data set.

United States Patent Application 20130106416 by Morich et al. published on May 2, 2013 with the title "ROUTER AND COIL ARRAY FOR ULTRA HIGH FIELD MRI", and is incorporated herein by reference. This publication 20130106416 describes a router for use with magnetic resonance systems that selectively routes unique excitation signals generated by a multi-channel radio-frequency (RF) amplifier over transmission lines (Tx) to any one of a plurality of connection panels which each accepts at least one RF coil assembly having multiple coil elements. Each connection panel includes transceiver ports for connecting at least one conductor of the coil elements to a corresponding transceiver channel (T/R). The router selectively routes magnetic resonance signals received by the conductors from the transceiver channels (T/R) to a multi-channel RF receiver. The coin elements may carry sine-mode currents or uniform currents.

There remains a long-felt need for improved SNR from received signals in an MRI system when imaging a relatively thin tissue sample.

SUMMARY OF THE INVENTION

In some embodiments, the present invention provides an apparatus and method for holding and rotating a tissue specimen in a magnetic-resonance system. This apparatus includes a first substrate having a first major surface and a second major surface; a first plurality of RF coils affixed to the first major surface of the first substrate; a plurality of signal conductors operatively coupled to the RF coils; a tissue enclosure configured to hold a slice of tissue; and a rotator operatively coupled to rotate the tissue enclosure around at least a first rotation axis.

In some embodiments, the present invention provides an overlapped array (RF) MRI coils that are optionally in a plane parallel to and near to a tissue-slice sample that is to be imaged or examined by MR spectroscopy.

In some embodiments, the present invention provides a method for holding and rotating a tissue specimen in a magnetic-resonance system. This method includes: providing a first plurality of RF coils affixed to a first major surface of a first substrate; providing a tissue enclosure; operatively coupling a plurality of signal conductors to the first plurality of RF coils; constraining a slice of tissue in the tissue enclosure; and rotating the tissue enclosure relative to the first plurality of RF coils around at least a first rotation axis.

BRIEF DESCRIPTION OF THE DRAWINGS

FIG. 1 is a block diagram of a sample-rotating MRI coil system 100 having a plurality of overlapping RF coil loops next to a tissue-slice sample, according to some embodiments of the present invention.

FIG. 2A is an exploded perspective-view diagram of a sample-rotating MRI coil subsystem 201 having a plurality of overlapping coil loops 218 each connected to one or more of a plurality of RF receiver-electronics systems (not shown), according to some embodiments of the present invention.

FIG. 5C is an exploded perspective-view diagram of a sample-rotating MRI coil subsystem 503 similar to system 502, according to some embodiments of the present invention.

DESCRIPTION OF PREFERRED EMBODIMENTS

Figure 2B:
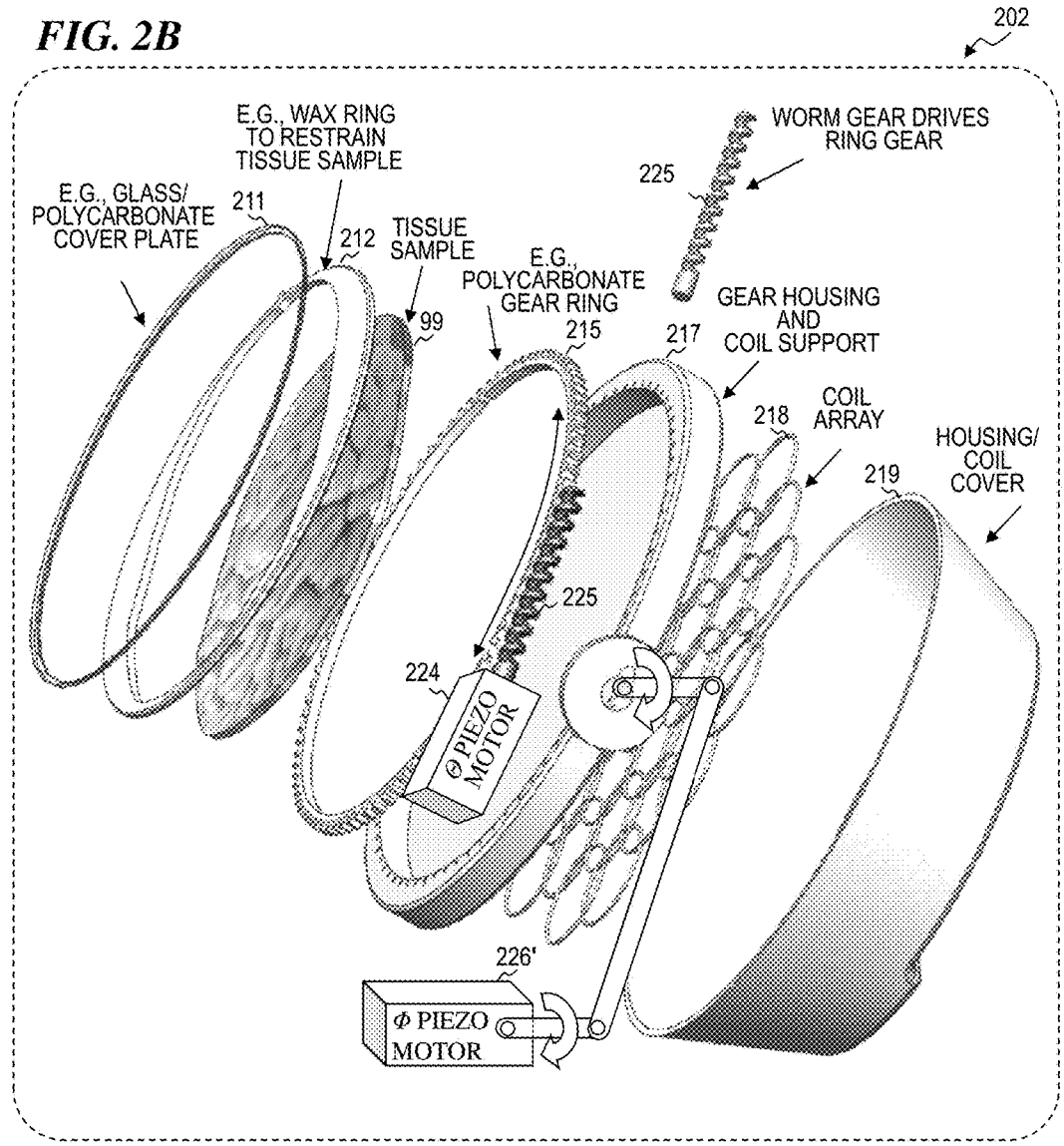
FIG. 2B is another exploded perspective-view diagram of a sample-rotating MRI coil subsystem 202 similar to system 201, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, a non-magnetic mechanical movement device is any electrically-controlled device (such as a linear positioner, rotary motor, or pump) made of materials that do not move (or move to a substantially negligible amount) due to a high magnetic field when subjected to the high magnetic field. Such devices can be placed within the high magnetic field of a magnetic-resonance machine or the superconducting magnet of a particle accelerator without the danger of the device moving due to the magnetic field and/or without the undesirable result of changing the magnetic field due to their presence. In many of the descriptions herein, the term "motor" (such as motor 140) will be used as an example of such a non-magnetic mechanical movement device, however one of skill in the art will recognize that in other embodiments, the "motor" can be implemented as a linear or rotary motor device using suitable linkages, or as a pump that uses a liquid or pneumatic fluid to effectuate the described movement.

It is to be understood that any of the combinations or subcombinations described below are examples that represent the invention and subsets and combinations of the described elements are also embodiments of the invention, and optionally one or more of the patents described above are combined with the elements and systems described below to form other embodiments of the present invention. The examples and combinations are not to be interpreted to limit the scope of the invention.

FIG. 1 is a block diagram of a sample-rotating MRI coil system and method 100 having a plurality of overlapping RF coil loops next to a tissue-slice sample, according to some embodiments of the present invention. In some embodiments, system 100 includes starting 101 the operations of obtaining a tissue sample 120, constraining and covering (enclosing) the sample next to RF MRI coils (e.g., in a slice container 210 that has or is next to the coils 218 (see FIG. 2A) on an outside planar surface of a substrate (e.g., on a gear housing and coil support 217, again see FIG. 2A) next to and facing the container), and iteratively rotating 124 the tissue sample (by rotating the container in a roll direction) relative to the coils 218 and taking images or spectroscopic data 134 at each of a plurality of different angular (roll) orientations of the sample 99 relative to the coils 218. In some embodiments, optional functions 126 and 136 rotate the sample in the pitch direction and obtain images at different pitch orientations relative to the DC magnetic field.

FIG. 2A is an exploded perspective-view diagram of a sample-rotating MRI coil subsystem 201 having a plurality of overlapping coil loops 218 each connected to one or more of a plurality of RF receiver-electronics systems 220, according to some embodiments of the present invention. In some embodiments, subsystem 201 includes a slice container 210 that includes a first face plate 211 (e.g., in various embodiments, glass, polycarbonate, or other suitable material) located on one side of sample 99 and removably attached a second face plate 215 on the opposite side of sample 99. In some embodiments, the second face plate 215 has a gear ring formed on a raised outer edge. In some embodiments, a tissue-support ring 212 made of wax or other suitable material has an inner edge (typically having an irregular shape made to conform to a support the outer edge of sample 99) and an outer edge shaped to conform to the inner edge of the gear ring of second face plate 215. In some embodiments, the thickness of the tissue slice and the thickness of the tissue-support ring are made to match the spacing between the inner surfaces of the first faceplate 211 and the second faceplate 215. In some embodiments, a microtome is configured such that an outer surface of a large tissue sample (e.g., such as an entire organ such as a brain) is frozen and coated with wax, the wax is carved to have an outer diameter that matches the inner diameter of the gear ring raised edge of second face plate 215, the second face plate 215 is placed over the tissue and its wax coating, and the tissue is then sliced by the microtome blade directly into the tissue-and-wax-ring space inside the raised edge of the second face plate 215. In some embodiments, this operation is performed with the second face plate 215 horizontal and with the microtome above it, such that the microtome is then lifted away and the first face plate 211 is fastened to the second face plate 215 to enclose the tissue sample 99. This assembled slice container 210 is then mounted inside gear housing 217 of subsystem 201. In some embodiments, a coil array 218 includes a plurality of coil loops arranged in a partially overlapped configuration on the back face of the gear housing 217 opposite the assembled slice container 210 and its enclosed tissue section 99. In some embodiments, a plurality of RF preamplifiers and/or RF transmit amplifiers and/or RF receive-transmit (RX-TX) switches are formed on or mounted to the back face of the gear housing 217 and are operatively coupled to the plurality of loops of the coil array 218. In some embodiments, gear housing 217 includes a worm gear 225 positioned to engage with the gear ring on the outer edge of slice container 210 to rotate the assembled slice container 210 and its enclosed tissue section 99 to one-at-a-time angular "roll-axis" position of a plurality of possible angular positions around roll-axis 88 relative to the coil array 218 in order that different portions of the tissue sample can be successively positioned over different loops of the coil array. In some embodiments, the center of the coil array (e.g., in some embodiments, the centermost loop) is offset relative to the rotational roll axis 88 (i.e., in some embodiments, each loop of the coil array 218 is at a different radial distance from the roll axis 88 of the tissue). In this way, a given portion of the tissue slice 99 can be positioned at different radial distances (i.e., and thus over a different loop that is a different distance relative to the center loop) by rotating that portion of tissue to a different rotational angle Θ around the roll axis 88. In some embodiments, a roll-axis motor 224 is driven by a controller to rotate the tissue sample 99 to a selected one of a plurality of different possible rotational angles Θ around the roll axis 88, and then maintain the sample at that angle while an MRI measurement and/or image is obtained. In some embodiments, a pitch-axis motor 226 is driven by a controller to rotate the tissue sample 99 to a selected pitch angle Φ around the roll axis 89 that, in some embodiments, is perpendicular to the roll axis 88, and then maintain the sample at that pitch angle Φ while an MRI measurement and/or image is obtained. In some embodiments, the other pieces of subsystem 201 are mounted in a housing/coil cover 219. In some embodiments, the circumferential side walls of housing/coil cover 219 are attached snugly to the outer edge of gear housing 217, while a back wall (not shown here—but see FIG. 5A and FIG. 5B) covers the coil array 218 and any electronics 220 of the TX and RX circuitry. In some embodiments, the majority of the control is performed in a separate (generally remote by several meters) control room computer system and electronics.

FIG. 2B is another exploded perspective-view diagram of a sample-rotating MRI coil subsystem 202 similar to system 201, according to some embodiments of the present invention. This subsystem 202 shows the roll-axis motor 224 and the pitch-axis motor 226 schematically. In some embodiments, the roll-axis motor 224 and the pitch-axis motor 226 are miniaturized such that they both fit within housing/coil cover 219. In some embodiments, the housing/coil cover 219 includes a plurality of external electrical connections (e.g., in some embodiments, on the back cover plane of housing/coil cover 219). In some embodiments, housing/coil cover 219 further includes RF shielding to limit and control the spatial extent of the RF field generated by coil array 218. Other aspects of FIG. 2B are as shown in FIG. 2A.

Figure 3:
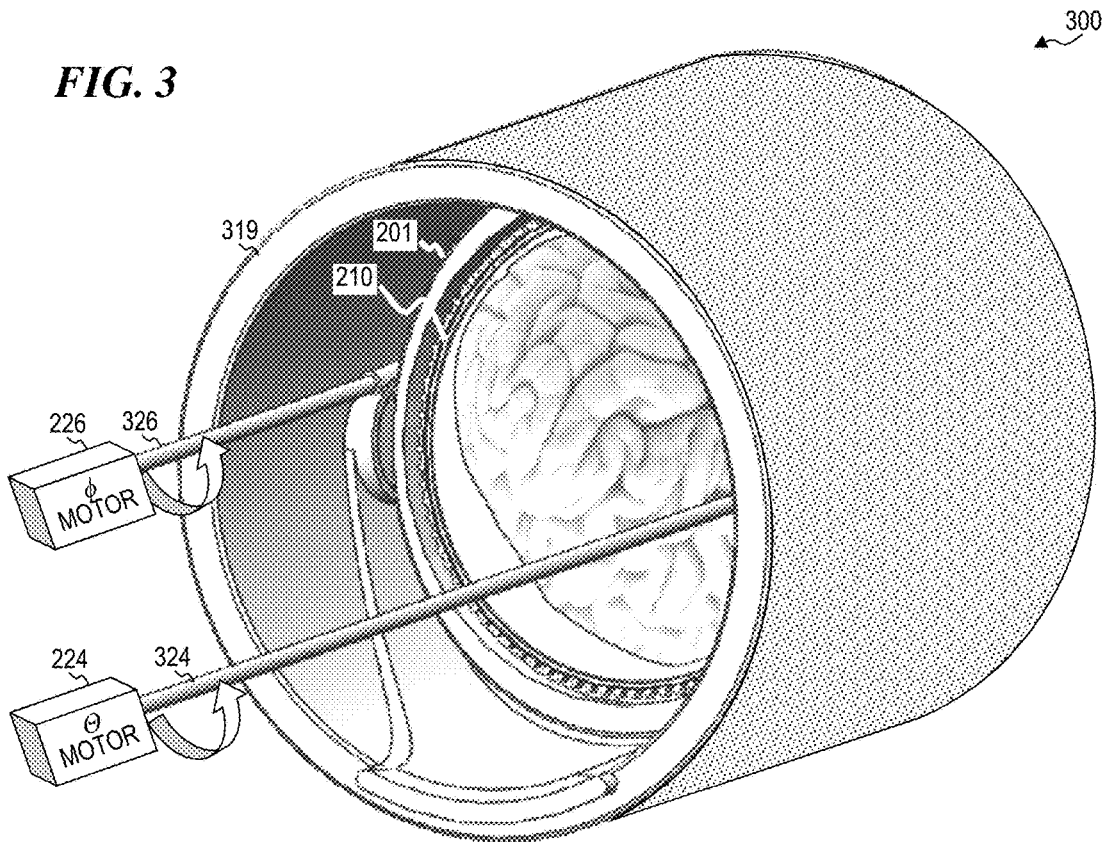
FIG. 3 is another perspective-view diagram of a sample-rotating MRI coil subsystem 300 that uses subsystem 201, according to some embodiments of the present invention.

FIG. 3 is another perspective-view diagram of a sample-rotating MRI coil subsystem 300 that, in some embodiments, uses subsystem 201, according to some embodiments of the present invention. In one such embodiment, the roll-axis motor 224 and the pitch-axis motor 226 are positioned outside of the bore of the MRI magnet (not shown here—but see 449 of FIG. 4). In some embodiments, a housing 319 is provided to hold subsystem 201 including tissue-slice holder 210; pitch-angle-adjustment shaft 326 connects pitch-axis motor 226 (located at a distance) to subsystem 201, and roll-angle-adjustment shaft 324 connects roll-axis motor 224 (located at a distance) to subsystem 201. In some embodiments, shaft 324 and shaft 326 are made of polycarbonate, ceramic, or other suitable non-magnetic and/or electrically insulating material. In some embodiments, housing 319 further includes RF shielding to limit and control the spatial extent of the RF field generated by coil array 218. Other aspects and reference numbers of FIG. 3 are as shown in FIG. 2A and described above.

Figure 4:
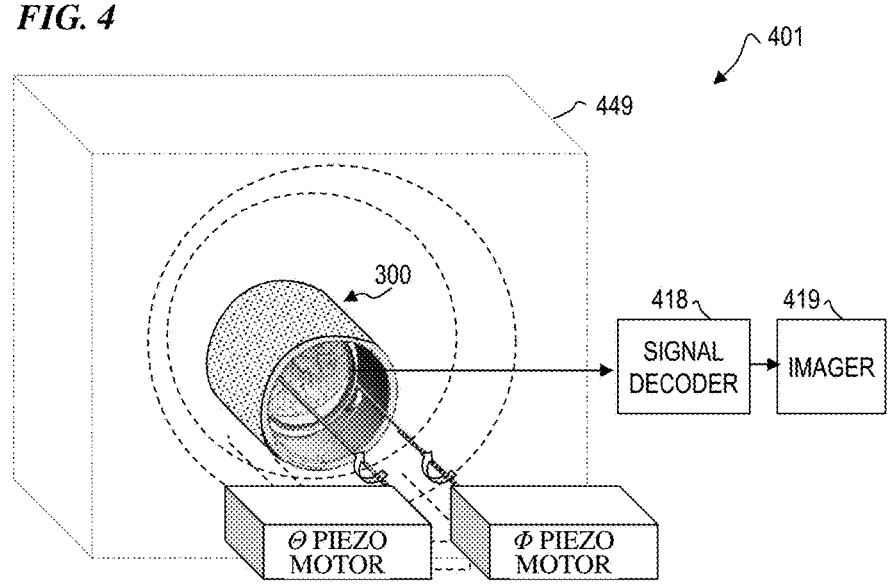
FIG. 4 is a perspective-view diagram of a sample-rotating MRI coil subsystem 300 in an MRI machine 449, according to some embodiments of the present invention.

FIG. 4 is a perspective-view diagram of a system 401 that includes sample-rotating MRI coil subsystem 300 in the bore of the magnet of an MRI machine 449, according to some embodiments of the present invention. In some embodiments, the pre-amplified receive signals from subsystem 201 are coupled to a signal decoder 418 (e.g., circuitry and/or one or more computers of the MRI controller that process the signals) and an imager 419 that outputs an image to be displayed and/or stored in a formatted file for later display, further processing, or other use. Other aspects and reference numbers of FIG. 4 are as shown in FIG. 3 and described above.

Figure 5A:
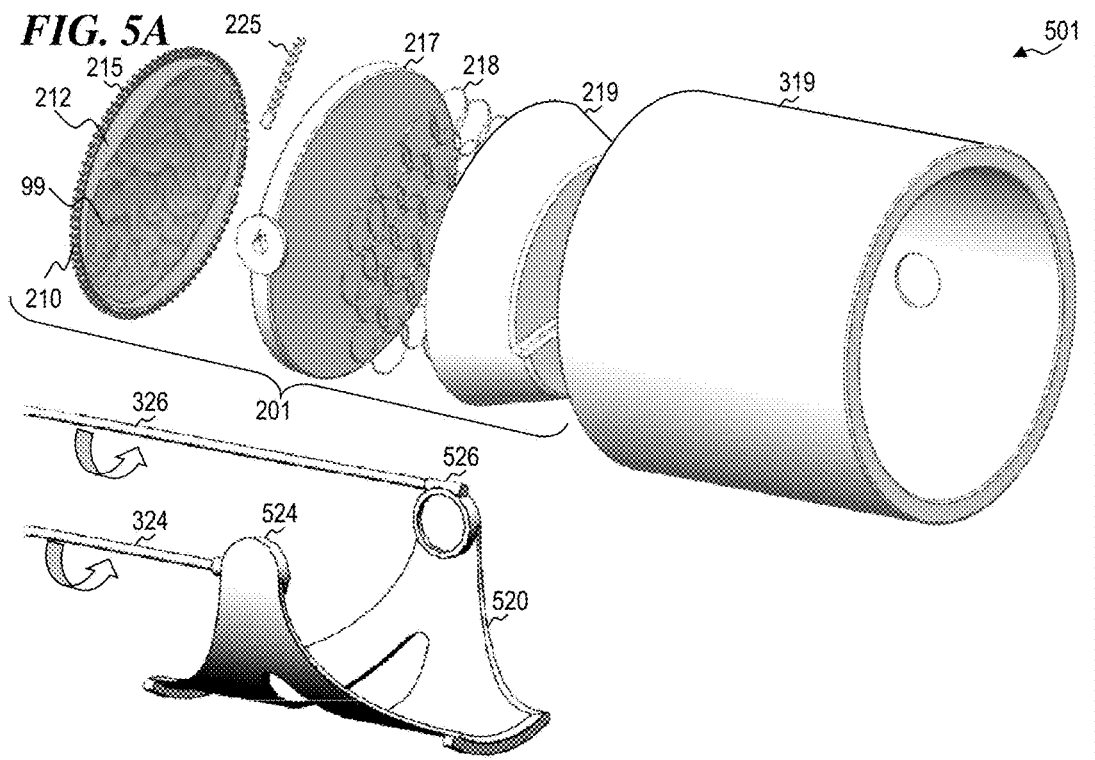
FIG. 5A is an exploded perspective-view diagram of a sample-rotating MRI coil subsystem 501 similar to system 300, according to some embodiments of the present invention.

FIG. 5A is an exploded perspective-view diagram of a sample-rotating MRI coil subsystem 501 substantially similar to system 300, according to some embodiments of the present invention. In some embodiments, subsystem 501 includes a cradle 520 that supports subsystem 201 within housing 319 and facilitates adjustment of the roll angle and pitch (vertical tilt and/or left-right rotation) angle. In some embodiments, cradle 520 includes a roll-gear assembly 524 that is driven by roll-angle-adjustment shaft 324 to adjust the roll angle of specimen holder 210 and thus the roll angle of specimen 99, and a pitch-gear assembly 526 that is driven by pitch-angle-adjustment shaft 326 to adjust the pitch (tilt) angle of specimen holder 210 and thus the pitch angle of specimen 99.

Figure 5B:
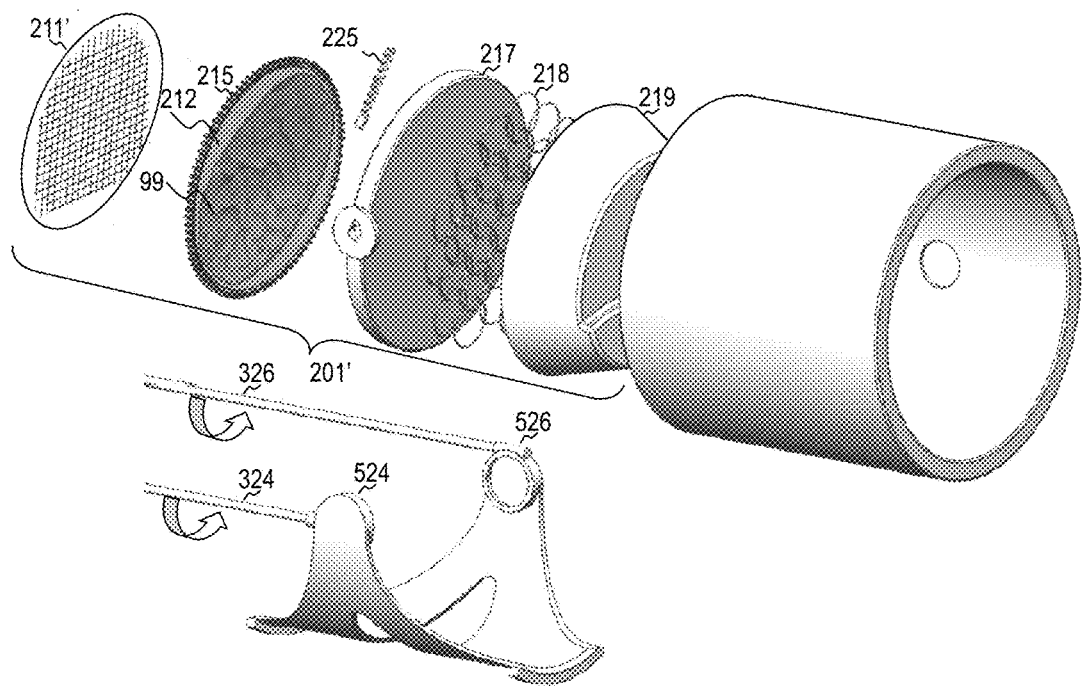
FIG. 5B is an exploded perspective-view diagram of a sample-rotating MRI coil subsystem 502 similar to system 501, according to some embodiments of the present invention.

FIG. 5B is an exploded perspective-view diagram of a sample-rotating MRI coil subsystem 502 similar to system 501, according to some embodiments of the present invention. In some embodiments, one difference between system 502 and system 501 is that in system 502 the subsystem 201' (which is substantially the same as system 201 except for the addition of a grid-plate feature 211' that provides both a visual metric for optical images of the tissue slice (including infrared, visible, ultraviolet and fluorescent images) and one that is apparent in MR images obtained from the specimen) is added to or part of the slice holder 210. In some embodiments, the optical images obtained at each of a plurality of different spectra and/or with each of a plurality of different fluorescent, antibody and/or other taggants or chemical markers, and the MR images are combined to determine tissue types and characteristics for each of a plurality of slices that are successively analyzed in subsystem 502 are assembled into a three-dimensional (3D) model showing detailed tissue types and other characteristics of the sliced specimens. In some such embodiments, the present invention includes methods and devices such as described in the journal article by G. J. Augustine titled "Combining patch clamp and optical methods in brain slices," Journal of Neuroscience methods 54 (1994) pp. 163-169, U.S. Pat. No. 7,295,870 to Allain et al. issued on Nov. 13, 2007 with the title "Method for the detection and automatic characterization of nodules in a tomographic image and a system of medical imaging by tomodensimetry" and/or United States Patent Application Publication 20070236490 by Casteele et al. published on Oct. 11, 2007 with the title "Medical image display and review system," each of which is incorporated herein by reference.

In some embodiments, grid-plate feature 211' also or alternatively provides a plurality of electrodes and/or optical fibers and/or chemical-delivery channels (connected to appropriate wires, optical fibers and/or tubing for fluids (liquid or gasses) at their distal ends and, at their proximal ends, operatively coupled or exposed to stimulate or sense physiological activity in the tissue slice 99) that are used to deliver selective electrical and/or optical and/or chemical stimulation or marking to different portions of the specimen, such that physiological changes over time can be observed optically (again, using imaging techniques (including with infrared, visible and/or ultraviolet light as well as fluorescent images with or without taggants), sensed electrically, and/or simultaneously or sequentially measured via magnetic-resonance spectroscopy/imaging to obtain in vitro functional MRI resulting from the one or more various types of electrical, optical fibers and/or chemical stimulation. In some embodiments, one or more various types of simulation of the neuronal tissue of the brain are utilized for the in vitro tissue slice using techniques and apparatus such as described in U.S. Pat. No. 8,788,044 to John issued on Jul. 22 2014 with the title "Systems and methods for tissue stimulation in medical treatment," which is incorporated herein by reference.

FIG. 5C is an exploded perspective-view diagram of a sample-rotating MRI coil subsystem 503 similar to system 502, according to some embodiments of the present invention. In some embodiments, system 503 further includes one or more drivers and/or sources and/or sensors and/or pre-amplifiers for sensors 518 for electrical stimulation, optical stimulation and/or chemical stimulation and/or marking. In some embodiments, grid plate 211' includes one or more electrodes, optrodes, optical fiber ports, fluid transport tubes, each operatively connected to the tissue slice at the proximal ends of wires, optical fibers, and/or fluid-transport tubes.

Figure 6A:
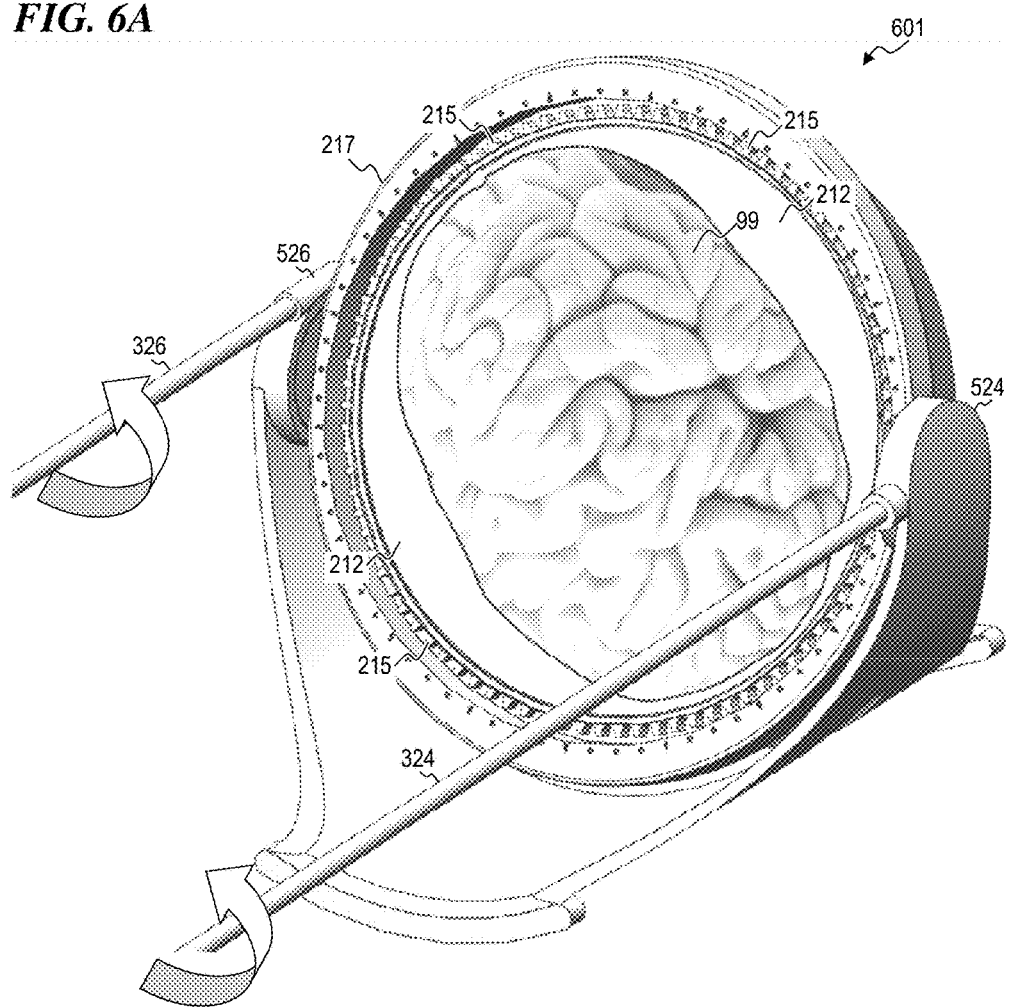
FIG. 6A is a perspective-view diagram of a sample-rotating MRI coil subsystem 601 similar to system 300, according to some embodiments of the present invention.

FIG. 6A is a detailed perspective-view diagram of a sample-rotating MRI coil subsystem 601 similar or identical to system 300, according to some embodiments of the present invention.

Figure 6B:
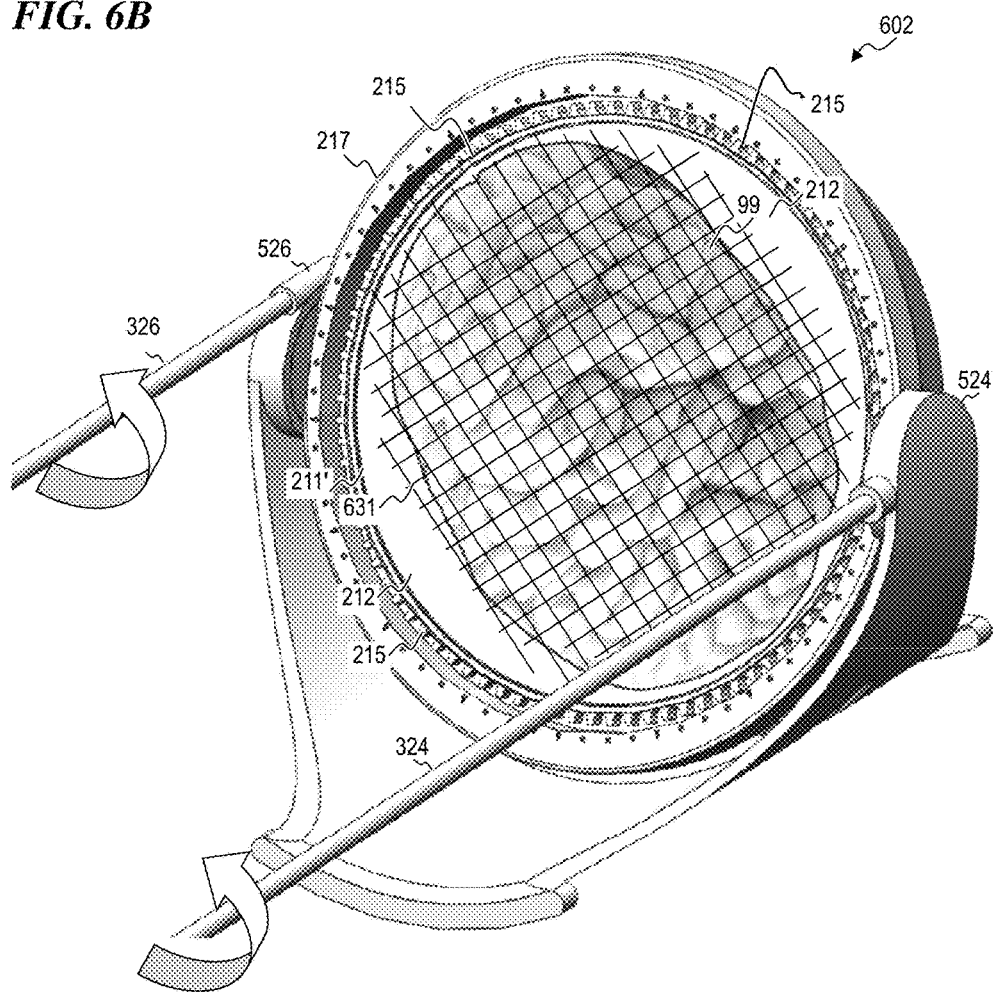
FIG. 6B is a perspective-view diagram of a sample-rotating MRI coil subsystem 602 similar to system 601, according to some embodiments of the present invention.

FIG. 6B is a perspective-view diagram of a sample-rotating MRI coil subsystem 602 similar to system 601, according to some embodiments of the present invention. In some embodiments, the primary difference is that system 602 includes grid plate 211'. In some embodiments, grid plate 211' includes a fiducial grid that is both optically visible (e.g., to various wavelengths of light) and visible as a fiducial marking in the MR images obtained. In some embodiments, grid plate 211' includes an array of electrical conductors and/or optical waveguides that are used to deliver stimulation signals and/or to receive sensed signals to a plurality of different locations on the specimen 99 (e.g., wherein one or more destinations or sources on the specimen can be selected at a time, and wherein a succession of stimulation signals can be sent and a succession of sensed results can be measured and recorded). In some embodiments, one or more fluid channels are connected to and arranged in grid plate 211' to carry fluids to deliver to, and/or receive from, the tissue-slice specimen 99.

Figure 7A:
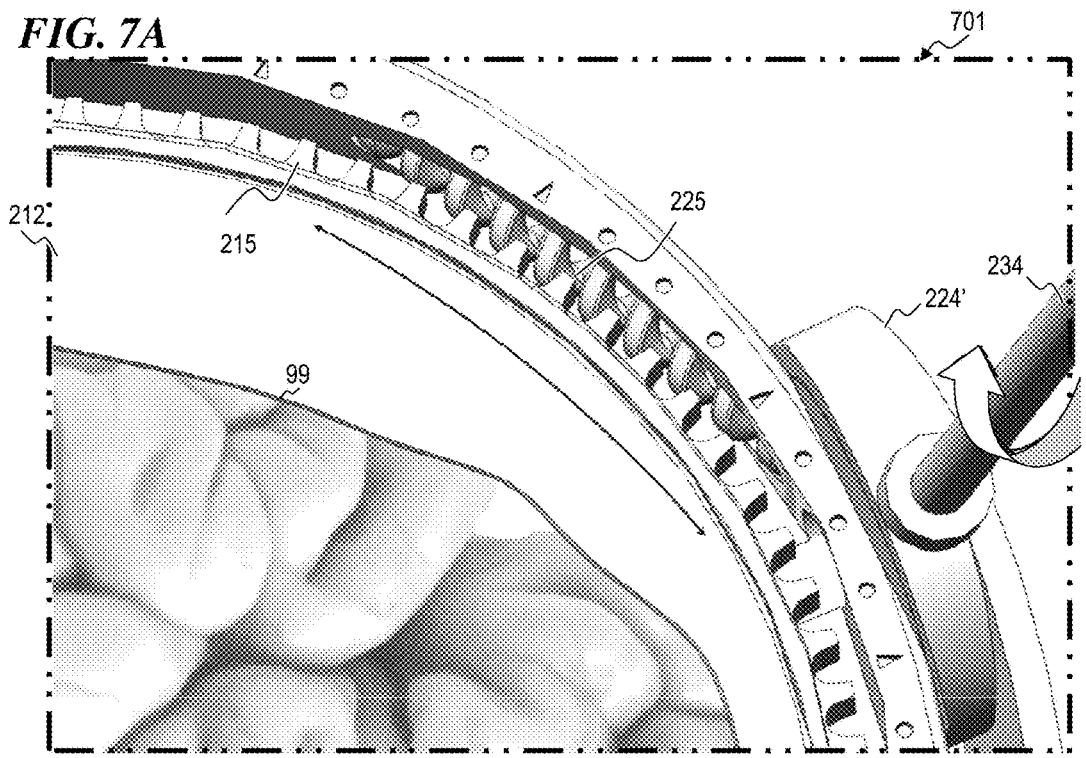
FIG. 7A is an enlarged perspective-view diagram of part of a sample-rotating MRI coil subsystem 701 similar to system 601, according to some embodiments of the present invention.

FIG. 7A is an enlarged perspective-view diagram of part of a sample-rotating MRI coil subsystem 701 similar to system 601, according to some embodiments of the present invention. In some embodiments, worm gear 225 engages with the outer-edge gear 215 to move the tissue-slice specimen 99 to the desired roll-angle position (e.g., in some embodiments, to locate a particular location/volume portion of the tissue in spatial relation to one or more of the loops of the coil array 218. In some embodiments, a piezo motor or other non-magnetic rotation actuator 224' is located within the edge housing and shaft 324 is omitted.

Figure 7B:
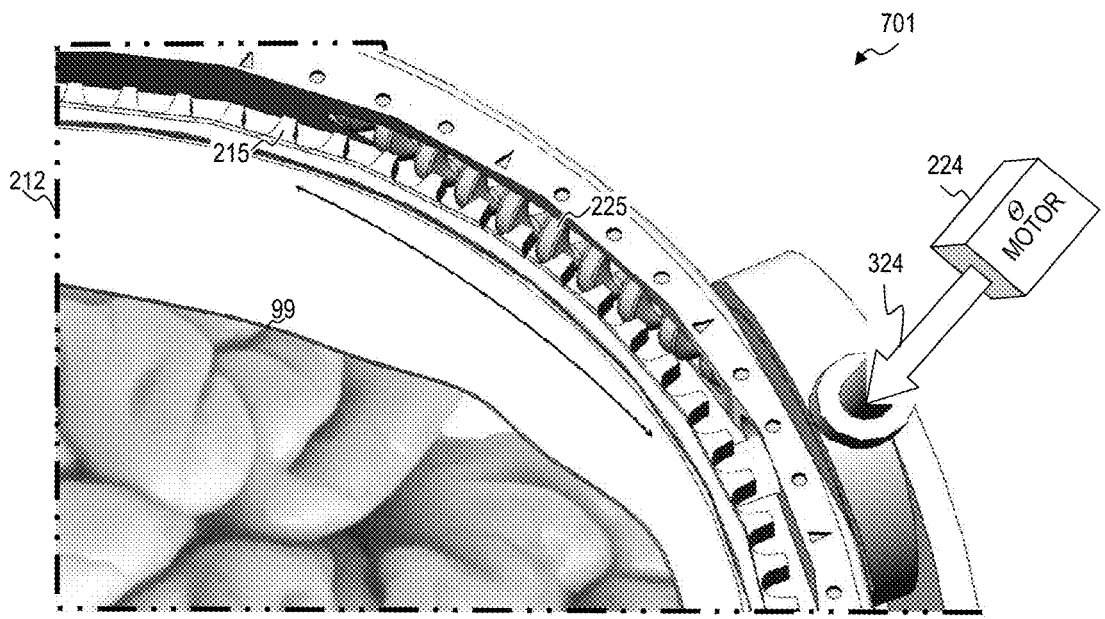
FIG. 7B is an enlarged perspective-view diagram of part of a sample-rotating MRI coil subsystem 702 similar to system 601, according to some embodiments of the present invention.

FIG. 7B is an enlarged perspective-view diagram of part of a sample-rotating MRI coil subsystem 702 similar to system 601, according to some embodiments of the present invention. In some embodiments, a piezo motor or other non-magnetic rotation actuator 224 is located at a distance from the housing on the side and shaft 324 is included.

Figure 8:
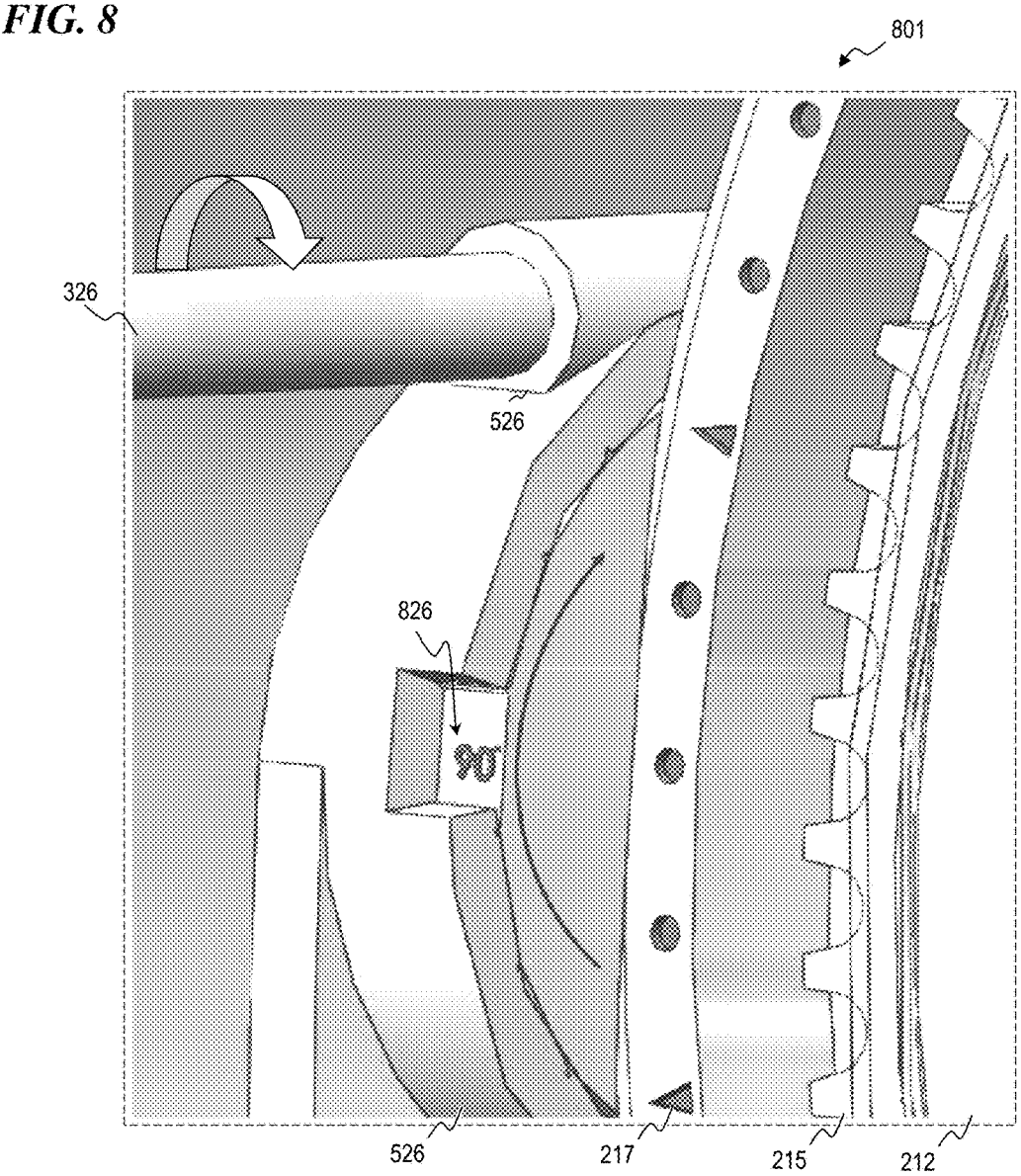
FIG. 8 is an enlarged perspective-view diagram of part of a sample-rotating MRI coil subsystem 801 similar to system 601, according to some embodiments of the present invention.

FIG. 8 is an enlarged perspective-view diagram of part of a sample-rotating MRI coil subsystem 801 similar to system 601, according to some embodiments of the present invention. In some embodiments, system 801 includes a digital indicator 826 of the pitch angle. In some embodiments, a similar digital indicator is provided on the opposite (e.g., right-hand) side for indicating the roll angle.

Figure 9:
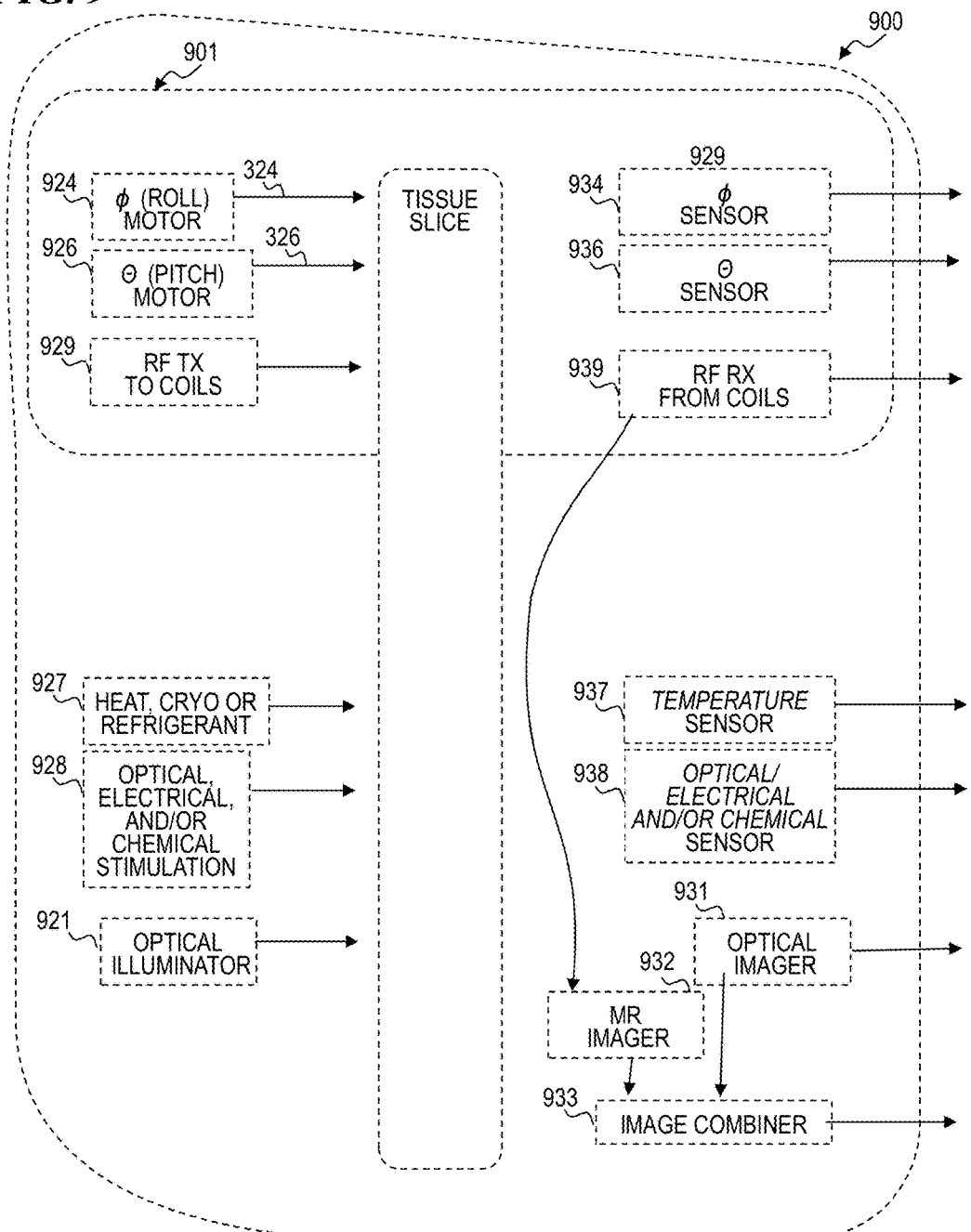
FIG. 9 is a block diagram of a system 900 that includes a sample-rotating MRI coil subsystem 901, according to some embodiments of the present invention.

FIG. 9 is a block diagram of a system 900 that includes a sample-rotating MRI coil subsystem 901, according to some embodiments of the present invention. In some embodiments, subsystem 901 provides a plurality of motors (for example, rotary of linear actuators; e.g., in some embodiments, piezo motors connected to nylon shafts) to rotate the tissue slice 99 sample in the roll (via motor 924) and/or pitch (via motor 926) angular directions. In some embodiments, system 900 and optionally subsystem 901, heats and/or cools via temperature-adjustment device 927 (including cryogenic cooling such as by using liquid nitrogen), provides electrical, optical and/or chemical stimulation to the sample via electrodes, optical waveguides, or fluid channels formed on the inside surface(s) of the sample container (e.g., on the glass or polycarbonate cover), and electrical circuit 929 does transmission (TX) of the RF signals to the coils, and optionally provides sensors for each (φ roll-angle sensor 934, Θ tilt-angle sensor 936, temperature sensor 937, electrical, optical, and/or chemical sensor(s) 938, and RF sensors 939 receive the MRI receive signals from the coil array 218). In some embodiments, system 900 further includes an optical illuminator 921 that provides a desired spectrum of light (such as infrared, visible, ultraviolet, narrowband (e.g., for inducing fluorescence), laser, stroboscopic, and/or the like), and an optical imager 931. Some embodiments further include a magnetic-resonance imager 932 that generates a series of one or more MR images based on the received RF signals from the plurality of coils/array of loops 218. Some embodiments further include an image combiner 933 that combines image data from optical imager 931 and magnetic-resonance imager 932. In some such embodiments, the fiducial indicia from cover plate 211' are used to correlate and align features from the optical imager data with features from the magnetic-resonance imager data to generate a combined image and/or to provide improved tissue characterization and typing.

In some embodiments, the present invention provides a non-transitory computer-readable medium having instructions stored thereon for causing a suitably programmed information processor to execute a method of the present invention.

In some embodiments, the present invention provides an apparatus for transmitting and/or receiving radio-frequency (RF) signals suitable for magnetic-resonance imaging (MRI) and/or magnetic-resonance spectroscopy (MRS) from radio-frequency (RF) coils that are overlapped and facing adjacent a rotatable tissue sample. In some embodiments, the apparatus includes a substrate having a first major surface and a second major surface; a first plurality of RF coils affixed to the first major surface of the substrate; a tissue enclosure facing the plurality of RF coils; and a tissue-sample rotator.

In some embodiments, the present invention provides an apparatus for holding and rotating a tissue specimen in a magnetic-resonance system. This apparatus includes a first substrate having a first major surface and a second major surface; a first plurality of RF coils affixed to the first major surface of the first substrate; a plurality of signal conductors operatively coupled to the RF coils; a tissue enclosure configured to hold a slice of tissue; and a rotator operatively coupled to rotate the tissue enclosure around at least a first rotation axis.

In some embodiments of the apparatus, the tissue enclosure is facing adjacent to the first substrate, wherein the first rotation axis is perpendicular to a plane of the first major surface.

In some embodiments of the apparatus, the first plurality of RF coils is arranged as an array of overlapping loops, wherein each one of a plurality of the loops overlaps six neighboring loops.

In some embodiments of the apparatus, the tissue enclosure includes a first planar plate and a second planar plate that is parallel to the first planar plate, and wherein the tissue enclosure is configured to hold the slice of tissue with a first major surface of the tissue in direct contact with the first planar plate and with a second major surface of the tissue, opposite the first major surface in direct contact with the second planar plate. In some embodiments, the first planar plate includes a plurality of fiducial markings that are visible to an optical imager and that are detectable by an MR imaging system. In some embodiments, the first planar plate includes a plurality of electrodes each configured to be in electrical contact with a different one of a plurality of separate locations on the slice of tissue. In some embodiments, the first planar plate includes a plurality of optical waveguides each configured to be in optical communication with a different one of a plurality of separate locations on the slice of tissue. In some embodiments, the first planar plate includes a plurality of fluid channels each configured to be in fluid communication with a different one of a plurality of separate locations on the slice of tissue. In some embodiments, the first planar plate includes a plurality of chemical sensors each configured to be in communication with a different one of a plurality of separate locations on the slice of tissue. In some embodiments, the first planar plate includes a temperature-control system operably configured to reduce a temperature of the slice of tissue. In some embodiments, the first planar plate includes a temperature-control system operably configured to adjustably control a temperature of the slice of tissue by selectively increasing and decreasing the temperature. In some embodiments, the first planar plate includes a Peltier-effect thermoelectric temperature-control system operably configured to adjustably control a temperature of the slice of tissue by selectively increasing and decreasing the temperature of the slice of tissue.

In some embodiments of the apparatus, the rotator is operatively coupled to rotate the tissue enclosure and the first plurality of RF coils relative to a second rotation axis that is parallel to the first major surface.

In some embodiments of the apparatus, the rotator includes a first non-magnetic rotary actuator configured to rotate the slice of tissue around the first rotation axis in a roll direction that is perpendicular to a major plane of the first plurality of RF coils; and a second non-magnetic rotary actuator configured to rotate the slice of tissue around a second axis that is perpendicular to the first rotation axis.

Some embodiments of the apparatus further include a plurality of receive-signal preamplifiers, wherein each one of the plurality of receive-signal preamplifiers is operatively coupled to receive RF signals from at least one of the first plurality of RF coils, and wherein the plurality of receive-signal preamplifiers is affixed to the first major surface of the first substrate.

Some embodiments of the apparatus further include a plurality of receive-signal preamplifiers operatively coupled to receive RF signals from the first plurality of RF coils, wherein the plurality of receive-signal preamplifiers is affixed to the first substrate.

Some embodiments of the apparatus further include a plurality of Rx/Tx switches and a plurality of preamplifiers operatively coupled to selectively receive RF signals through the plurality of Rx/Tx switches from the first plurality of RF coils when in a receive mode, wherein the plurality of Rx/Tx switches and the plurality of preamplifiers are affixed to the first substrate, and wherein the plurality of Rx/Tx switches is configured to deliver a plurality of transmit signals to the first plurality of RF coils when in a transmit mode.

Some embodiments of the apparatus further include a plurality of transmit amplifiers affixed to the first substrate; a plurality of Rx/Tx switches affixed to the first substrate; and a plurality of receive-signal preamplifiers operatively coupled to selectively receive RF signals through the plurality of Rx/Tx switches from the first plurality of RF coils when in a receive mode, wherein the plurality of Rx/Tx switches and the plurality of preamplifiers are affixed to the first substrate, and wherein the plurality of Rx/Tx switches is configured to deliver a plurality of transmit signals to the first plurality of RF coils when in a transmit mode.

Some embodiments of the apparatus further include a second plurality of RF coils operatively configured to transmit RF signals useful for magnetic-resonance measurements, wherein the first plurality of RF coils is operatively configured to receive RF signals useful for magnetic-resonance measurements.

Some embodiments of the apparatus further include a controller operatively coupled to the rotator to successively rotate the slice of tissue to each one of a plurality of roll angles and to obtain a magnetic-resonance image of the slice of tissue at each one of the plurality of roll angles.

Some embodiments of the apparatus further include a controller operatively coupled to the rotator to successively rotate the slice of tissue in a roll direction around the first rotational axis to each one of a plurality of roll angles, and to independently successively rotate the slice of tissue around a second axis perpendicular to the roll axis to each one of a plurality of angles relative to the second axis, and wherein the controller is configured to obtain a magnetic-resonance image of the slice of tissue at each one of the plurality of roll angles, and to obtain a magnetic-resonance image of the slice of tissue at each one of the plurality of angles relative to the second axis.

In some embodiments, the tissue enclosure includes a ring gear oriented in a circular path around a roll axis, and wherein the rotator includes a worm gear operatively configured to engage the ring gear to rotate the slice of tissue around the roll axis.

In some embodiments, the present invention provides a method for holding and rotating a tissue specimen in a magnetic-resonance system. This method includes: providing a first plurality of RF coils affixed to a first major surface of a first substrate; providing a tissue enclosure; operatively coupling a plurality of signal conductors to the first plurality of RF coils; constraining a slice of tissue in the tissue enclosure; and rotating the tissue enclosure relative to the first plurality of RF coils around at least a first rotation axis.

Some embodiments of the method further include connecting the tissue enclosure to be facing adjacent to the first substrate, wherein a plane defined by each loop of the array of loops is substantially parallel to a plane of the first major surface, and wherein the first rotation axis is perpendicular to the plane of first major surface.

In some embodiments of the method, the first plurality of RF coils is arranged as an array of overlapping loops, and each one of a plurality of the loops overlaps six neighboring loops.

In some embodiments of the method, the tissue enclosure includes a first planar plate and a second planar plate that is parallel to the first planar plate, and the constraining of the slice of tissue includes holding the slice of tissue with a first major surface of the tissue in direct contact with the first planar plate and with a second major surface of the tissue, opposite the first major surface in direct contact with the second planar plate.

In some embodiments of the method, the first planar plate includes a plurality of fiducial markings, and the method further includes: obtaining an optical image of the slice of tissue such that indicia of the fiducial markings are visible in the optical image; obtaining a magnetic-resonance image of the slice of tissue such that indicia of the fiducial markings are visible in the magnetic-resonance image; and generating a combined image of the slice of tissue that uses the indicia of the fiducial markings and that includes data from the optical image and data from the magnetic-resonance image.

In some embodiments of the method, the first planar plate includes a plurality of electrodes each configured to be in electrical contact with a different one of a plurality of separate locations on the slice of tissue, and the method further includes: transmitting electrical-stimulation signals to the slice of tissue via the plurality of electrodes.

In some embodiments of the method, the first planar plate includes a plurality of electrodes each configured to be in electrical contact with a different one of a plurality of separate locations on the slice of tissue, and the method further includes receiving electrical signals from the slice of tissue via the plurality of electrodes.

In some embodiments of the method, the first planar plate includes a plurality of optical waveguides each configured to be in optical communication with a different one of a plurality of separate locations on the slice of tissue, and the method further includes transmitting optical-stimulation signals to the slice of tissue via the plurality of optical waveguides.

In some embodiments of the method, the first planar plate includes a plurality of optical waveguides each configured to be in optical communication with a different one of a plurality of separate locations on the slice of tissue, and the method further includes receiving optical signals from the slice of tissue via the plurality of optical waveguides.

In some embodiments of the method, the first planar plate includes a plurality of fluid channels each configured to be in fluid communication with a different one of a plurality of separate locations on the slice of tissue, and the method further includes transmitting chemicals to the slice of tissue via the plurality of fluid channels.

In some embodiments of the method, the first planar plate includes a plurality of fluid channels each configured to be in fluid communication with a different one of a plurality of separate locations on the slice of tissue, and the method further includes receiving chemicals from the slice of tissue via the plurality of fluid channels.

In some embodiments of the method, the first planar plate includes a plurality of chemical sensors each configured to be in communication with a different one of a plurality of separate locations on the slice of tissue, and the method further includes detecting chemicals from the slice of tissue via the plurality of plurality of chemical sensors.

In some embodiments of the method, the first planar plate includes a temperature-control system, and the method further includes reducing a temperature of the slice of tissue.

In some embodiments of the method, the first planar plate includes a temperature-control system, and the method further includes adjustably controlling a temperature of the slice of tissue by selectively increasing and decreasing the temperature.

In some embodiments of the method, the first planar plate includes a Peltier temperature-control system, and the method further includes adjustably controlling a temperature of the slice of tissue by selectively increasing and decreasing the temperature.

Some embodiments of the method further include rotating the tissue enclosure and the first plurality of RF coils around a second rotation axis that is parallel to the first major surface.

Some embodiments of the method further include rotating the slice of tissue around the first rotation axis in a roll direction relative to a major plane of the first plurality of RF coils; and rotating the slice of tissue around a second axis that is perpendicular to the first rotation axis.

Some embodiments of the method further include providing a plurality of receive-signal preamplifiers affixed to the first major surface of the first substrate, wherein each one of the plurality of receive-signal preamplifiers is operatively coupled to receive RF signals from at least one of the first plurality of RF coils; and preamplifying received signals from the first plurality of RF coils using the plurality of receive-signal preamplifiers.

Some embodiments of the method further include providing a plurality of receive-signal preamplifiers affixed to the first substrate; and amplifying RF signals from the first plurality of RF coils using the plurality of receive-signal preamplifiers.

Some embodiments of the method further include providing a plurality of receive-signal preamplifiers affixed to the first major surface of the first substrate; providing a plurality of Rx/Tx switches affixed to the first major surface of the first substrate; amplifying RF signals coupled through the plurality of Rx/Tx switches from the first plurality of RF coils to the plurality of receive-signal preamplifiers when in a receive mode; and delivering a plurality of transmit signals through the plurality of Rx/Tx switches to the first plurality of RF coils when in a transmit mode.

Some embodiments of the method further include providing a plurality of receive-signal preamplifiers affixed to the first major surface of the first substrate; providing a plurality of transmit-signal amplifiers affixed to the first major surface of the first substrate; providing a plurality of Rx/Tx switches affixed to the first major surface of the first substrate; amplifying, with the plurality of receive-signal preamplifiers, RF signals coupled through the plurality of Rx/Tx switches from the first plurality of RF coils to the plurality of receive-signal preamplifiers when in a receive mode; and amplifying, with the plurality of transmit-signal amplifiers, a plurality of transmit signals and coupling the amplified transmit signals through the plurality of Rx/Tx switches to the first plurality of RF coils when in a transmit mode.

Some embodiments of the method further include providing a second plurality of RF coils affixed to the first substrate; transmitting RF signals useful for magnetic-resonance measurements using the second plurality of RF coils; and receiving RF signals useful for magnetic-resonance measurements using the first plurality of RF coils.

Some embodiments of the method further include successively rotating the slice of tissue to each one of a plurality of roll angles; and obtaining a magnetic-resonance image of the slice of tissue at each one of the plurality of roll angles.

Some embodiments of the method further include successively rotating the slice of tissue around a roll axis to each one of a plurality of roll angles; obtaining a magnetic-resonance image of the slice of tissue at each one of the plurality of roll angles; successively rotating the slice of tissue around a second axis perpendicular to the roll axis to each one of a plurality of angles relative to the second axis; and obtaining a magnetic-resonance image of the slice of tissue at each one of the plurality of angles relative to the second axis.

In some embodiments of the method, the tissue enclosure includes a ring gear oriented in a circular path around the roll axis, and the method further includes engaging a worm gear to the ring gear to rotate the slice of tissue around the roll axis.

In some embodiments, the present invention provides an apparatus for holding and rotating a tissue specimen in a magnetic-resonance system. This apparatus includes: a first plurality of RF coils affixed to a first major surface of a first substrate; a tissue enclosure; means for operatively coupling a plurality of signal conductors to the first plurality of RF coils; means for constraining a slice of tissue in the tissue enclosure (e.g., including cover plate 211 or cover plate 211' having fiducial markings, electrodes, optical waveguides, chemical sensors, or fluid-transporting passageways); and means for rotating the tissue enclosure relative to the first plurality of RF coils around at least a first rotation axis (e.g., devices such as shaft 234, shaft 236, motor 224, motor 226, ring gear 215, worm gear 225, and/or the like).

Some embodiments of this apparatus further includes means for connecting the tissue enclosure to be facing adjacent to the first substrate, wherein a plane defined by each loop of the array of loops is substantially parallel to a plane of the first major surface, and wherein the first rotation axis is perpendicular to the plane of first major surface.

In some embodiments of this apparatus, the first plurality of RF coils is arranged as an array of overlapping loops, and each one of a plurality of the loops overlaps six neighboring loops.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of fiducial markings, and wherein the apparatus further includes: means for obtaining an optical image of the slice of tissue such that indicia of the fiducial markings are visible in the optical image; means for obtaining a magnetic-resonance image of the slice of tissue such that indicia of the fiducial markings are visible in the magnetic-resonance image; and means for generating a combined image of the slice of tissue that uses the indicia of the fiducial markings and that includes data from the optical image and data from the magnetic-resonance image.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of electrodes each configured to be in electrical contact with a different one of a plurality of separate locations on the slice of tissue, and wherein the apparatus further includes: means for transmitting electrical-stimulation signals to the slice of tissue via the plurality of electrodes.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of electrodes each configured to be in electrical contact with a different one of a plurality of separate locations on the slice of tissue, and wherein the apparatus further includes means for receiving electrical signals from the slice of tissue via the plurality of electrodes.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of optical waveguides each configured to be in optical communication with a different one of a plurality of separate locations on the slice of tissue, and wherein the apparatus further includes means for transmitting optical-stimulation signals to the slice of tissue via the plurality of optical waveguides.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of optical waveguides each configured to be in optical communication with a different one of a plurality of separate locations on the slice of tissue, and wherein the apparatus further includes means for receiving optical signals from the slice of tissue via the plurality of optical waveguides.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of fluid channels each configured to be in fluid communication with a different one of a plurality of separate locations on the slice of tissue, and wherein the apparatus further includes means for transmitting chemicals to the slice of tissue via the plurality of fluid channels.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of fluid channels each configured to be in fluid communication with a different one of a plurality of separate locations on the slice of tissue, and wherein the apparatus further includes means for receiving chemicals from the slice of tissue via the plurality of fluid channels.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a plurality of chemical sensors each configured to be in communication with a different one of a plurality of separate locations on the slice of tissue, and wherein the apparatus further includes means for detecting chemicals from the slice of tissue via the plurality of plurality of chemical sensors.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, wherein the first planar plate includes a temperature-control system, and wherein the apparatus further includes means for reducing a temperature of the slice of tissue.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, and the first planar plate includes a temperature-control system, and wherein the apparatus further includes means for adjustably controlling a temperature of the slice of tissue by selectively increasing and decreasing the temperature.

In some embodiments of this apparatus, the tissue enclosure includes a first planar plate and a second planar plate that is parallel to the first planar plate, wherein the means for constraining the slice of tissue includes means for holding the slice of tissue with a first major surface of the tissue in direct contact with the first planar plate and with a second major surface of the tissue, opposite the first major surface in direct contact with the second planar plate, and the first planar plate includes a Peltier temperature-control system, and wherein the apparatus further includes means for adjustably controlling a temperature of the slice of tissue by selectively increasing and decreasing the temperature.

Some embodiments of the apparatus further include means for rotating the tissue enclosure and the first plurality of RF coils around a second rotation axis that is parallel to the first major surface.

Some embodiments of the apparatus further include means for rotating the slice of tissue around the first rotation axis in a roll direction relative to a major plane of the first plurality of RF coils; and means for rotating the slice of tissue around a second axis that is perpendicular to the first rotation axis.

Some embodiments of the apparatus further include a plurality of receive-signal preamplifiers affixed to the first major surface of the first substrate, wherein each one of the plurality of receive-signal preamplifiers is operatively coupled to receive RF signals from at least one of the first plurality of RF coils; and means for preamplifying received signals from the first plurality of RF coils using the plurality of receive-signal preamplifiers.

Some embodiments of the apparatus further include a plurality of receive-signal preamplifiers affixed to the first substrate; and means for amplifying RF signals from the first plurality of RF coils using the plurality of receive-signal preamplifiers.

Some embodiments of the apparatus further include a plurality of receive-signal preamplifiers affixed to the first major surface of the first substrate; a plurality of Rx/Tx switches affixed to the first major surface of the first substrate; means for amplifying RF signals coupled through the plurality of Rx/Tx switches from the first plurality of RF coils to the plurality of receive-signal preamplifiers when in a receive mode; and means for delivering a plurality of transmit signals through the plurality of Rx/Tx switches to the first plurality of RF coils when in a transmit mode.

Some embodiments of the apparatus further include a plurality of receive-signal preamplifiers affixed to the first major surface of the first substrate; a plurality of transmit-signal amplifiers affixed to the first major surface of the first substrate; a plurality of Rx/Tx switches affixed to the first major surface of the first substrate; means for amplifying, with the plurality of receive-signal preamplifiers, RF signals coupled through the plurality of Rx/Tx switches from the first plurality of RF coils to the plurality of receive-signal preamplifiers when in a receive mode; and means for amplifying, with the plurality of transmit-signal amplifiers, a plurality of transmit signals and coupling the amplified transmit signals through the plurality of Rx/Tx switches to the first plurality of RF coils when in a transmit mode.

Some embodiments of the apparatus further include a second plurality of RF coils affixed to the first substrate; means for transmitting RF signals useful for magnetic-resonance measurements using the second plurality of RF coils; and means for receiving RF signals useful for magnetic-resonance measurements using the first plurality of RF coils.

Some embodiments of the apparatus further include means for successively rotating the slice of tissue to each one of a plurality of roll angles; and means for obtaining a magnetic-resonance image of the slice of tissue at each one of the plurality of roll angles.

Some embodiments of the apparatus further include means for successively rotating the slice of tissue around a roll axis to each one of a plurality of roll angles; means for obtaining a magnetic-resonance image of the slice of tissue at each one of the plurality of roll angles; means for successively rotating the slice of tissue around a second axis perpendicular to the roll axis to each one of a plurality of angles relative to the second axis; and means for obtaining a magnetic-resonance image of the slice of tissue at each one of the plurality of angles relative to the second axis.

In some embodiments, the tissue enclosure includes a ring gear oriented in a circular path around the roll axis, and the apparatus further includes means for engaging a worm gear to the ring gear to rotate the slice of tissue around the roll axis.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," " "second," and "third," etc., are used merely as labels, and are not intended to impose numerical requirements on their objects.

What is claimed is:

1. An apparatus for holding and rotating a tissue specimen in a magnetic-resonance system, the apparatus comprising:
   a first substrate having a first major surface;
   a first plurality of RF coils affixed to the first major surface of the first substrate;
   a plurality of signal conductors operatively coupled to the first plurality of RF coils;
   a tissue enclosure configured to hold a slice of tissue; and
   a rotator operatively coupled to rotate the tissue enclosure, relative to the first plurality of RF coils, around at least a first rotation axis.

2. The apparatus of claim 1, wherein the tissue enclosure is facing adjacent to the first substrate, wherein the first rotation axis is perpendicular to a plane of the first major surface.

3. The apparatus of claim 1, wherein the first plurality of RF coils is arranged as an array of overlapping loops, wherein a plane defined by each loop of the array of loops is substantially parallel to a plane of the first major surface, and wherein each one of a plurality of the loops overlaps six neighboring loops.

4. The apparatus of claim 1, wherein the tissue enclosure includes a first planar plate and a second planar plate that is parallel to the first planar plate, and wherein the tissue enclosure is configured to hold the slice of tissue with a first major surface of the tissue in direct contact with the first planar plate and with a second major surface of the tissue, opposite the first major surface in direct contact with the second planar plate.

5. The apparatus of claim 1, wherein the tissue enclosure includes a first planar plate and a second planar plate that is parallel to the first planar plate, and wherein the tissue enclosure is configured to hold the slice of tissue with a first major surface of the tissue in direct contact with the first planar plate and with a second major surface of the tissue, opposite the first major surface in direct contact with the second planar plate, wherein the first planar plate includes a plurality of fiducial markings that are visible to an optical imager and that are detectable by an MR imaging system.

6. The apparatus of claim 1, wherein the tissue enclosure includes a first planar plate and a second planar plate that is parallel to the first planar plate, and wherein the tissue enclosure is configured to hold the slice of tissue with a first major surface of the tissue in direct contact with the first planar plate and with a second major surface of the tissue, opposite the first major surface in direct contact with the second planar plate, wherein the first planar plate includes a plurality of electrodes each configured to be in electrical contact with a different one of a plurality of separate locations on the slice of tissue.

7. The apparatus of claim 1, wherein the rotator includes
   a first non-magnetic rotary actuator configured to rotate the slice of tissue around the first rotation axis in a roll direction that is perpendicular to a major plane of the first plurality of RF coils; and
   a second non-magnetic rotary actuator configured to rotate the slice of tissue around a second axis that is perpendicular to the first rotation axis.

8. The apparatus of claim 1, further comprising a plurality of receive-signal preamplifiers, wherein each one of the plurality of receive-signal preamplifiers is operatively coupled to receive RF signals from at least one of the first plurality of RF coils, and wherein the plurality of receive-signal preamplifiers is affixed to the first major surface of the first substrate.

9. The apparatus of claim 1, further comprising:
   a plurality of transmit amplifiers affixed to the first substrate;
   a plurality of receive-signal preamplifiers affixed to the first substrate; and
   a plurality of Rx/Tx switches affixed to the first substrate and operatively coupled to selectively receive RF signals through the plurality of Rx/Tx switches from the first plurality of RF coils when in a receive mode, and wherein the plurality of Rx/Tx switches is configured to deliver a plurality of transmit signals to the first plurality of RF coils when in a transmit mode.

10. The apparatus of claim 1, further comprising a controller operatively coupled to the rotator to successively rotate the slice of tissue around a roll axis to each one of a plurality of roll angles and to obtain a magnetic-resonance image of the slice of tissue at each one of the plurality of roll angles, and to successively rotate the slice of tissue around a second axis perpendicular to the roll axis to each one of a plurality of angles relative to the second axis and to obtain a magnetic-resonance image of the slice of tissue at each one of the plurality of angles relative to the second axis.

11. The apparatus of claim 1, wherein the tissue enclosure includes a ring gear oriented in a circular path around a roll axis, and wherein the rotator includes a worm gear operatively configured to engage the ring gear to rotate the slice of tissue around the roll axis.

12. A method for holding and rotating a tissue specimen in a magnetic-resonance system, the method comprising:
providing a first plurality of RF coils affixed to a first major surface of a first substrate;
providing a tissue enclosure;
operatively coupling a plurality of signal conductors to the first plurality of RF coils;
constraining a slice of tissue in the tissue enclosure; and
rotating the tissue enclosure relative to the first plurality of RF coils around at least a first rotation axis.

13. The method of claim 12, wherein the first plurality of RF coils is arranged as an array of overlapping loops, and wherein each one of a plurality of the loops overlaps six neighboring loops.

14. The method of claim 12, wherein the tissue enclosure includes a first planar plate and a second planar plate that is parallel to the first planar plate, wherein the first planar plate includes a plurality of fiducial markings, and wherein the method further includes:
obtaining an optical image of the slice of tissue such that indicia of the fiducial markings are visible in the optical image;
obtaining a magnetic-resonance image of the slice of tissue such that indicia of the fiducial markings are visible in the magnetic-resonance image; and
generating a combined image of the slice of tissue that uses the indicia of the fiducial markings and that includes data from the optical image and data from the magnetic-resonance image.

15. The method of claim 12, wherein the first planar plate includes a temperature-control system, and wherein the method further includes adjustably controlling a temperature of the slice of tissue by selectively increasing and decreasing the temperature.

16. The method of claim 12, further comprising:
rotating the slice of tissue around the first rotation axis in a roll direction relative to a major plane of the first plurality of RF coils; and
rotating the slice of tissue around a second axis that is perpendicular to the first rotation axis.

17. The method of claim 12, further comprising:
providing a plurality of receive-signal preamplifiers affixed to the first major surface of the first substrate;
providing a plurality of transmit-signal amplifiers affixed to the first major surface of the first substrate;
providing a plurality of Rx/Tx switches affixed to the first major surface of the first substrate;
amplifying, with the plurality of receive-signal preamplifiers, RF signals coupled through the plurality of Rx/Tx switches from the first plurality of RF coils to the plurality of receive-signal preamplifiers when in a receive mode; and
amplifying, with the plurality of transmit-signal amplifiers, a plurality of transmit signals and coupling the amplified transmit signals through the plurality of Rx/Tx switches to the first plurality of RF coils when in a transmit mode.

18. The method of claim 12, further comprising:
successively rotating the slice of tissue around a roll axis to each one of a plurality of roll angles;
obtaining a magnetic-resonance image of the slice of tissue at each one of the plurality of roll angles;
successively rotating the slice of tissue around a second axis perpendicular to the roll axis to each one of a plurality of angles relative to the second axis; and
obtaining a magnetic-resonance image of the slice of tissue at each one of the plurality of angles relative to the second axis.

19. The method of claim 12, further comprising:
successively rotating the slice of tissue around a roll axis to each one of a plurality of roll angles;
obtaining a magnetic-resonance image of the slice of tissue at each one of the plurality of roll angles;
obtaining an optical image of the slice of tissue; and
combining data from at least one of the magnetic-resonance images of the slice of tissue and the optical image of the slice of tissue to obtain a combined image that includes data from both the at least one magnetic-resonance image and the optical image.

20. An apparatus for holding and rotating a tissue specimen in a magnetic-resonance system, the apparatus comprising:
a first plurality of RF coils affixed to a first major surface of a first substrate;
a tissue enclosure;
means for operatively coupling a plurality of signal conductors to the first plurality of RF coils;
means for constraining a slice of tissue in the tissue enclosure; and
means for rotating the tissue enclosure relative to the first plurality of RF coils around at least a first rotation axis.

21. The apparatus of claim 1, wherein the tissue slice held by the tissue enclosure is a slice across an entire organ and is surrounded by wax.

22. The apparatus of claim 1, wherein the tissue slice held by the tissue enclosure is a slice across an entire organ and is surrounded by wax, and wherein an outer diameter of the wax matches an inner diameter of the tissue enclosure.

23. The apparatus of claim 1, wherein the tissue enclosure includes a first face plate, a second face plate and a gear ring around a circumference of the second face plate, wherein the first face plate, second face plate and gear ring are assembled to form a slice container.

24. The apparatus of claim 1, wherein the tissue enclosure is facing adjacent to the first substrate, wherein the first rotation axis is perpendicular to a plane of the first major surface, wherein the first plurality of RF coils is arranged as an array of overlapping loops, and wherein a plane defined by each loop of the array of loops is substantially parallel to a plane of the first major surface, and wherein each one of a plurality of the loops overlaps six neighboring loops.

* * * * *